US008798966B1

(12) United States Patent  
Hench et al.

(10) Patent No.: US 8,798,966 B1  
(45) Date of Patent: Aug. 5, 2014

(54) MEASURING CRITICAL DIMENSIONS OF A SEMICONDUCTOR STRUCTURE

(75) Inventors: John Hench, Los Gatos, CA (US);  
Daniel Wack, Los Altos, CA (US);  
Edward Ratner, Sunnyvale, CA (US);  
Yaoming Shi, San Ramon, CA (US);  
Andrei Veldman, Issaquah, WA (US)

(73) Assignee: KLA-Tencor Corporation, Milpitas, CA (US)

( * ) Notice: Subject to any disclaimer, the term of this patent is extended or adjusted under 35 U.S.C. 154(b) by 855 days.

(21) Appl. No.: 11/648,965

(22) Filed: Jan. 3, 2007

(51) Int. Cl.
*G06F 17/50* (2006.01)
*G06F 7/60* (2006.01)
*G06F 13/10* (2006.01)
*G06F 11/26* (2006.01)

(52) U.S. Cl.
CPC ............ *G06F 13/105* (2013.01); *G06F 11/261* (2013.01); *G06F 17/50* (2013.01)
USPC .................................................. 703/2; 703/1

(58) Field of Classification Search
None
See application file for complete search history.

(56) References Cited

U.S. PATENT DOCUMENTS

| | | | |
|---|---|---|---|
| 6,483,580 B1* | 11/2002 | Xu et al. ........................ 356/300 |
| 6,664,121 B2* | 12/2003 | Grodnensky et al. ........... 438/16 |
| 6,782,337 B2 | 8/2004 | Wack et al. | |
| 6,839,126 B2* | 1/2005 | Yen et al. ........................ 355/68 |
| 7,092,110 B2* | 8/2006 | Balasubramanian et al. 356/625 |
| 7,115,858 B1* | 10/2006 | Holden et al. ................ 250/225 |
| 7,126,700 B2* | 10/2006 | Bao et al. ........................ 356/625 |
| 7,171,284 B2* | 1/2007 | Vuong et al. .................. 700/121 |
| 7,245,356 B2* | 7/2007 | Hansen ............................ 355/67 |
| 7,305,322 B2* | 12/2007 | Funk et al. ..................... 702/155 |
| 7,330,279 B2* | 2/2008 | Vuong et al. .................. 356/625 |
| 7,355,728 B2* | 4/2008 | Li et al. ........................... 356/625 |
| 7,363,611 B2* | 4/2008 | Rosenbluth ..................... 430/30 |
| 7,372,565 B1* | 5/2008 | Holden et al. ................ 356/327 |
| 7,388,677 B2* | 6/2008 | Vuong et al. .................. 356/601 |
| 7,391,524 B1* | 6/2008 | Chen et al. ..................... 356/625 |
| 7,451,054 B2* | 11/2008 | Deshpande et al. .......... 702/134 |
| 7,487,053 B2* | 2/2009 | Funk et al. ....................... 702/66 |
| 7,495,781 B2* | 2/2009 | Vuong et al. .................. 356/625 |
| 7,505,153 B2* | 3/2009 | Vuong et al. .................. 356/625 |
| 7,523,076 B2* | 4/2009 | Drege et al. ..................... 706/12 |
| 7,525,672 B1* | 4/2009 | Chen et al. ..................... 356/625 |
| 7,525,673 B2* | 4/2009 | Vuong et al. .................. 356/625 |

(Continued)

OTHER PUBLICATIONS

J. Elschner et al. in "Numerical Solution of Optimal Design Problems for Binary Gratings", Journal of Computational Physics, vol. 146, pp. 603-626, 1998.*

(Continued)

*Primary Examiner* — Shambhavi Patel
(74) *Attorney, Agent, or Firm* — Okamoto & Benedicto LLP

(57) ABSTRACT

One embodiment relates to a method of model-based optical metrology. An area of a geometrical structure of dispersive materials on a substrate is illuminated with polarized incident electromagnetic radiation using an illuminator of a scatterometer apparatus. Spectral components of the incident electromagnetic radiation reflected from the area are measured using a detector of the scatterometer apparatus. Using a computer for the scatterometer apparatus, parameter values are determined that minimize an objective function which represents a difference between the measured spectral components and computed spectral components based on a parameterized model of the geometrical structure. Steps for determining the parameter values that minimize the objective function include: computing a solution to state equations driven by a function representing the incident electromagnetic radiation, and computing a solution to an adjoint to the state equations. Other embodiments and features are also disclosed.

35 Claims, 11 Drawing Sheets

(56) References Cited

U.S. PATENT DOCUMENTS

| | | | |
|---|---|---|---|
| 7,526,354 B2* | 4/2009 | Madriaga et al. | 700/98 |
| 7,532,317 B2* | 5/2009 | Smith et al. | 356/237.2 |
| 7,555,395 B2* | 6/2009 | Willis et al. | 702/81 |
| 7,571,074 B2* | 8/2009 | Funk et al. | 702/170 |
| 7,588,949 B2* | 9/2009 | Vuong et al. | 438/16 |
| 7,616,325 B2* | 11/2009 | Vuong et al. | 356/601 |
| 7,751,046 B2* | 7/2010 | Levy et al. | 356/401 |
| 7,763,404 B2* | 7/2010 | Willis et al. | 430/30 |
| 7,831,528 B2* | 11/2010 | Doddi et al. | 706/12 |
| 8,179,530 B2* | 5/2012 | Levy et al. | 356/401 |
| 8,577,820 B2* | 11/2013 | Jin et al. | 706/19 |
| 2003/0215965 A1* | 11/2003 | Grodnensky et al. | 438/16 |
| 2004/0008353 A1* | 1/2004 | Chu | 356/636 |
| 2004/0017574 A1* | 1/2004 | Vuong et al. | 356/625 |
| 2004/0017575 A1* | 1/2004 | Balasubramanian et al. | 356/625 |
| 2004/0267397 A1* | 12/2004 | Doddi et al. | 700/110 |
| 2005/0128489 A1* | 6/2005 | Bao et al. | 356/601 |
| 2005/0192914 A1* | 9/2005 | Drege et al. | 706/12 |
| 2005/0209816 A1* | 9/2005 | Vuong et al. | 702/167 |
| 2005/0251771 A1* | 11/2005 | Robles | 716/5 |
| 2006/0064280 A1* | 3/2006 | Vuong et al. | 702/182 |
| 2006/0146347 A1* | 7/2006 | Smith et al. | 356/601 |
| 2006/0187466 A1* | 8/2006 | Li et al. | 356/601 |
| 2006/0290947 A1* | 12/2006 | Li et al. | 356/625 |
| 2007/0100591 A1* | 5/2007 | Harazaki | 703/2 |
| 2008/0074677 A1* | 3/2008 | Willis et al. | 356/601 |
| 2008/0074678 A1* | 3/2008 | Willis et al. | 356/601 |
| 2008/0076046 A1* | 3/2008 | Willis et al. | 430/30 |
| 2008/0077352 A1* | 3/2008 | Willis et al. | 702/155 |
| 2008/0195342 A1* | 8/2008 | Li et al. | 702/82 |
| 2009/0306941 A1* | 12/2009 | Kotelyanskii et al. | 703/1 |
| 2010/0233599 A1* | 9/2010 | Hinnen et al. | 430/30 |
| 2012/0086940 A1* | 4/2012 | Shih et al. | 356/307 |
| 2013/0222795 A1* | 8/2013 | Madsen et al. | 356/237.5 |
| 2014/0032463 A1* | 1/2014 | Jin et al. | 706/25 |

OTHER PUBLICATIONS

H. Gross et al. in "Mathematical modeling of indirect measurements in scatterometry", Measurement: Journal of the International Measurement Confederation, vol. 39, No. 9, Nov. 2006, pp. 782-794.*

Ioannis T. Rekanos in "Inverse Scattering in the Time Domain: An Iterative Method Using an FDTD Sensitivity Analysis Scheme", IEEE Transactions on Magnetics, vol. 38, No. 2, Mar. 2002, pp. 1117-1120.*

C. Altman et al. in "Eigenmode Scattering Relations for Plane-Stratified Gyrotropic Media", Applied Physics A: Materials Science & Processing, vol. 19, No. 2, Jun. 1979, Springer Berlin/Heidelberg, pp. 213-219.*

S.V. Vasil'ev, "Efficient diffraction grating for use in a grazing-incidence configuration", Quantum Electronics, vol. 28, No. 5, 1998, pp. 429-432.*

* cited by examiner

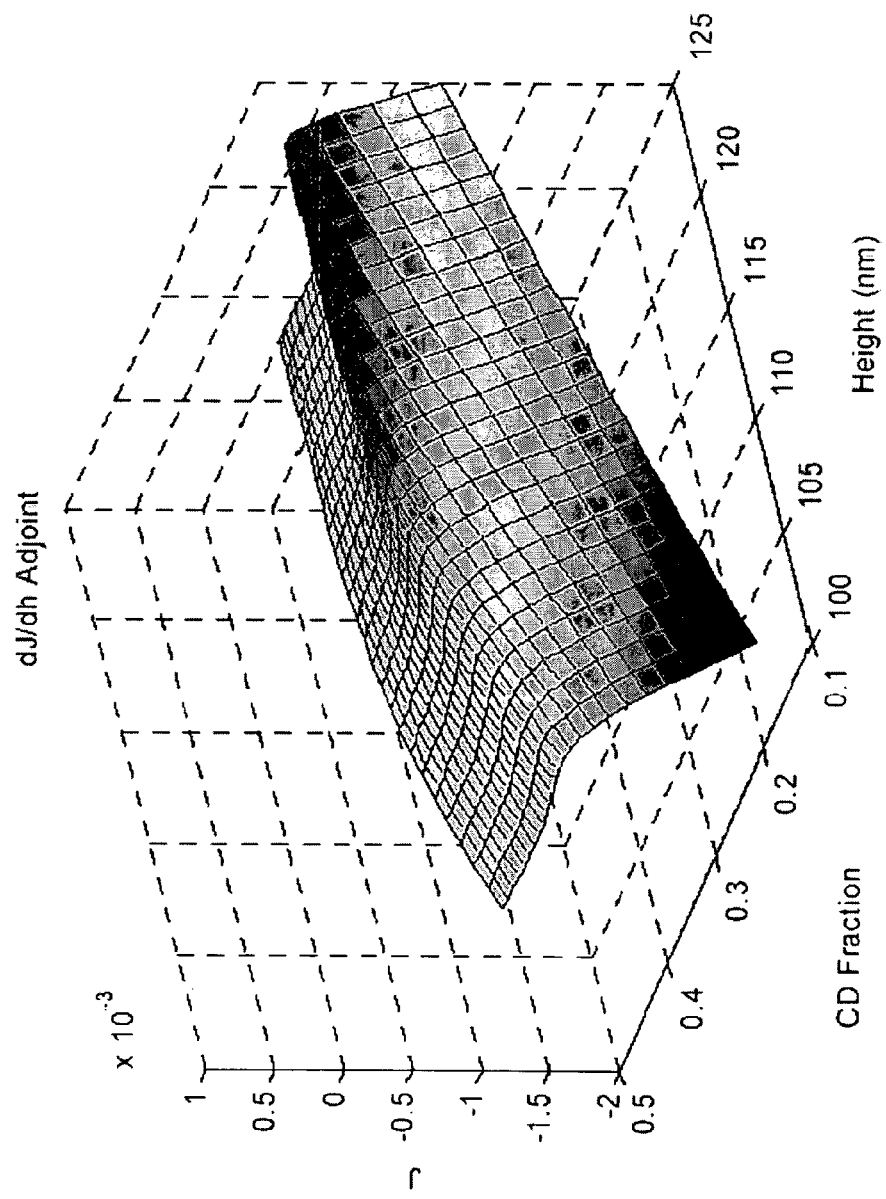

Time Domain

MEASURING CRITICAL DIMENSIONS OF A SEMICONDUCTOR STRUCTURE

BACKGROUND

The subject matter described herein generally relates to a method and apparatus for determining sensitivities of reflection or transmission spectra to various grating parameters via a time or frequency domain simulation. The computation of these sensitivities may be central in a number of techniques used in optically based metrology tools to deduce the features on semiconductor wafers.

Some metrology tools measure more than just one-dimensional critical dimension (CD) features, because of smaller device dimensions and tighter process control windows. It has become critical to efficiently detect, identify, and measure changes in feature profiles to control current and future semiconductor lithography and etch processes.

Generally, the determination of sensitivities of reflection or transmission spectra to various grating parameters via a time or frequency domain simulation has used a finite difference approximation of the derivatives.

The method of computing derivatives by finite differences has a number of disadvantages. For example, each desired derivative with respect to a single scalar parameter requires an additional solution of Maxwell's Equation. This computation can be costly, and as a result limits the total number of derivatives that may be computed for application where computation time is important. The computation cost also limits the number of wavelengths from the optical scattering data that may be processed, which prevents the use of the full information provided by the optical scattering data.

SUMMARY

One embodiment of the invention relates to a method of model-based metrology. An area of a geometrical structure of dispersive materials is illuminated with incident electromagnetic radiation, wherein the incident electromagnetic radiation is polarized, and spectral components of the incident electromagnetic radiation reflected from the area are measured. A determination is made as to parameter values that minimize an objective function which represents a difference between the measured spectral components and computed spectral components based on a parameterized model of the geometrical structure.

Another embodiment of the invention relates to an apparatus for metrology. The apparatus includes at least a polarized illuminator, a detector, and a data processing system. The polarized illuminator is configured to illuminate an area of a geometrical structure of dispersive materials with incident polarized electromagnetic radiation, and the detector is configured to measure spectral components of the incident electromagnetic radiation reflected from the area. The data processing system is configured to determine parameter values that minimize an objective function which represents a difference between the measured spectral components and computed spectral components based on a parameterized model of the geometrical structure.

Another embodiment relates to a method for estimating a critical dimension from spectroscopic measurements. The method includes computing a solution to state equations driven by a function representing the incident electromagnetic radiation, and computing a solution to an adjoint to the state equations. Such computations may be made using regression, or a library, or a combination of regression and a library. Advantageously, the time to compute each iteration of the solution at a given level of accuracy scales slower with an increasing number of parameters than computing each iteration of the solution at the given level of accuracy by finite difference derivatives.

Another embodiment relates to a method of computation to estimate a critical dimension from spectroscopic measurements, wherein with an increasing number of parameters N, a computation time per iteration at a given level of accuracy increases at a rate slower than N to the third power. In a preferred embodiment, the computation time per iteration at a given level of accuracy increases linearly with N.

Other embodiments and features are also disclosed.

BRIEF DESCRIPTION OF THE DRAWINGS

The accompanying drawings are included to provide further understanding of embodiments of the invention, illustrate various embodiments of the invention, and together with the description serve to explain the principles and operation of the invention.

FIGS. 4A through 4D are surface plots of derivatives, numerical and adjoint, in accordance with an embodiment of the present invention.

DETAILED DESCRIPTION

Introduction

Figure 1:
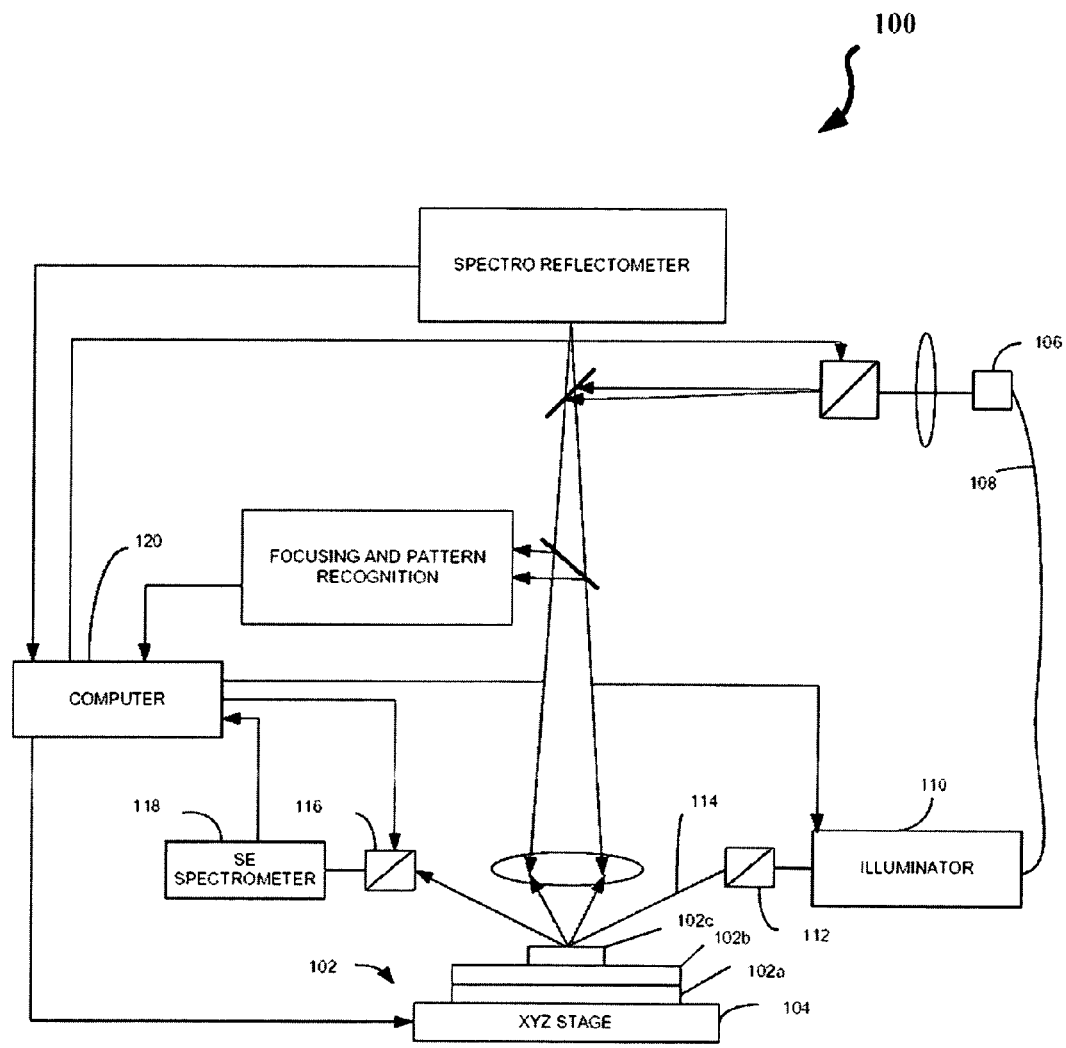
FIG. 1 is a schematic view of an embodiment of a representative spectroscopic scatterometer system.

Some embodiments of the present invention provide a mechanism for measuring critical dimensions (CD) in "grating" structures on semiconductor substrates, such as semiconductor wafers, using a technique called Optical CD (OCD). The mechanism minimizes an objective function that is a difference (typically mean square) between physical measurements of diffracted spectra and those that may be computed for a given parameterized description of the grating structure. The minimization procedure, referred to generally as regression, uses derivatives of the objective and/or measurement function with regard to the geometric parameters describing the grating.

In accordance with one embodiment of the invention, a method includes computing the spectra from a solution of the Maxwell's equations. The solution may be done broadly in at least two ways, first, using a frequency domain computation, one example of which is the Rigorous Coupled Wave Analysis (RCWA) method; and second, using a time domain computation.

The adjoint methods disclosed herein and described below provide for the computation of objective or measurement function derivatives with regard to geometric parameters more quickly and accurately than other methods; thus, speeding up the regression process. Furthermore, the same techniques may be used to find sensitivities of the measurements to optical parameters, such as wavelength, angle of incidence, azimuth angle, pitch, and index of refraction. The results may be used to optimize the signal-to-noise ratio of the measurement or to provide information about the precision of the estimate.

In one embodiment of the invention, the adjoint methods include five computations. The first computation is called the state solution. The state solution includes the computation of the measured reflection and transmission spectra of a grating on a semiconductor wafer via the solution to Maxwell's equations. The source function of these equations is a function describing the incident light.

The second computation is called the adjoint solution. The adjoint solution is the computation of the solution to a set of equations related to state equations. The source function for these equations is a function describing the derivative or first variation of the objective or measurement function as a function of the solution of the state equation.

The third computation is that of parametric derivatives due to perturbations of the state and/or adjoint equations.

The fourth computation is an inner-product like functional involving the state and adjoint solutions, where the inner-product functional depends on the parametric derivatives. The result of the fourth computation are derivatives of local parameters, such as a set of slab heights and slab CD fractions, or on optical parameters, such as wavelength, angle of incidence, azimuth angle, pitch, and index of refraction.

The result of the fifth computation is the compaction of the linear map between the local parameters and geometric parameters, such as trapezoid height, width, and wall angle.

Typically, the state computation may be time-intensive to perform, while the adjoint, derivative and inner-product computations are generally less so. For example, for the RCWA based 2D and 3D frequency domain Maxwell's equations solver, the computation time of the state solution scales as the third power of the number of Fourier modes describing the index of refraction of the grating. The adjoint, derivative and inner-product computations scale as the second power of the Fourier modes.

In various embodiments, the time and/or frequency domain methods may more quickly compute the derivatives of the measurement function with regard to geometric parameters that define the grating; thus, enabling higher order parameterization of a grating. Additionally, these derivatives may be computed more accurately than, for example, a finite-difference type method.

In various embodiments, the time and frequency domain methods may provide for is that the computation of measurements sensitivities allows the measurement setup to be optimized, maximizing measured signal as a function of, for example, wavelength, angle of incidence, and the like. By computing measurement derivatives, the reflection or transmission coefficients may be interpolated or extrapolated to neighboring values of incidence angle using Taylor's expansion or a cubic spline; which may be applied in numerical aperture averaging. Computing measurement derivatives may also enable faster computation of spectra in a wavelength neighborhood about the originally computed spectra in the case of the frequency domain solution.

Additional advantages, objects and features of embodiments of the invention are set forth in part in the detailed description which follows. It is to be understood that both the foregoing general description and the following detailed description are merely exemplary of embodiments of the invention, and are intended to provide an overview or framework for understanding the nature and character of embodiments of the invention.

In the previous discussion it was noted that if derivatives could be computed much faster than the spectra, then the computational speed of regression algorithms that require derivatives would be greatly increased. This is due to the fact that finite difference derivatives would not be need to be computed, which require an extra computation (forward solve) per dimension.

Another way in which the fast computation of derivatives would be advantageous would be in the production of a measurement library. A measurement library starts with a parameterization of a particular structure on a semiconductor wafer, and a volume in parameter space over which the parameters are expected to be varied. A measurement library is a collection of spectra computed at various nodes in parameter space. Once a library is generated, multidimensional polynomial models may be constructed for each spectrum, where the polynomial support is related to the parameterization of the structure. If these multidimensional polynomial models are sufficiently accurate, they may be used in place of the actual forward solves within regression. This significantly increases the speed of the regression, which eliminates a computational time bottleneck within the CD measurement process. In other words, the cost of the forward solve is paid in advance in the computation of the library, not during measurement. Nevertheless, it is also important to reduce the time it takes to compute the library, and the ability to compute derivative more quickly than the spectra can help in this regard.

To motivate this discussion, we start with a simple one dimensional example. Suppose we have a model of a semiconductor feature for which only the total height is unknown. Suppose, too, that the height is expected to vary from 100 nm to 130 nm, and that the dependence of the spectra, $\alpha$ and $\beta$ is smooth enough that a cubic model sufficiently captures its behavior over 30 nm intervals.

In such a case, we could build two cubic polynomial models, $$\alpha(p) = \alpha_0 + \alpha_1 p + \alpha_2 p^2 + \alpha_3 p^3$$
$$\beta(p) = \beta_0 + \beta_1 p + \beta_2 p^2 + \beta_3 p^3$$

for $\alpha$ and $\beta$, to cover the region in parameter space from p=100 to p=130 nm.

If we had only the spectra available (and not the derivatives) we would have to build a library consisting of the evaluation of $\alpha$ and $\beta$ at four nodes, e.g., [100 110 120 130]. The coefficients would be computed in the linear system, AX=B, where each row of the matrix A is row vector $r_A$ formed by appropriately exponentiating the parameter value, p $$r_A(p) = [\begin{array}{cccc} 1 & p & p^2 & p^3 \end{array}]$$

and where each row $r_B$ in the matrix B is the spectra associated with the particular parameter value $$r_B(p) = [\alpha(p), \beta(p)]$$

In the example above, the coefficients of the cubic spectra models would be computed by solving the following linear system:

$$\begin{bmatrix} 1 & 100 & 100^2 & 100^3 \\ 1 & 110 & 110^2 & 110^3 \\ 1 & 120 & 120^2 & 120^3 \\ 1 & 130 & 130^2 & 130^3 \end{bmatrix} \begin{bmatrix} \alpha_0 & \beta_0 \\ \alpha_1 & \beta_1 \\ \alpha_2 & \beta_2 \\ \alpha_3 & \beta_3 \end{bmatrix} = \begin{bmatrix} \alpha(100) & \beta(100) \\ \alpha(110) & \beta(110) \\ \alpha(120) & \beta(120) \\ \alpha(130) & \beta(130) \end{bmatrix}$$

If, however, we have derivatives available, we need only compute spectra and their derivatives at two nodes, e.g., [100 130]. In this case the linear system would be comprised of two-row blocks, $R_A$, in the matrix A for each parameter value $$R_A(p) = \begin{bmatrix} 1 & p & p^2 & p^3 \\ 0 & 1 & 2p & 3p^3 \end{bmatrix}$$

as well as two-row blocks, $R_B$, matrix B is the spectra associated with the particular parameter value $$R_B(p) = \begin{bmatrix} \alpha(p) & \beta(p) \\ \dfrac{d\alpha}{dp}(p) & \dfrac{d\beta}{dp}(p) \end{bmatrix}$$

In the example above, the coefficients would be computed by solving the following linear system:

$$\begin{bmatrix} 1 & 100 & 100^2 & 100^3 \\ 0 & 1 & 2 \cdot 100 & 3 \cdot 100^2 \\ 1 & 130 & 130^2 & 130^3 \\ 0 & 1 & 2 \cdot 130 & 3 \cdot 130^2 \end{bmatrix} \begin{bmatrix} \alpha_0 & \beta_0 \\ \alpha_1 & \beta_1 \\ \alpha_2 & \beta_2 \\ \alpha_3 & \beta_3 \end{bmatrix} = \begin{bmatrix} \alpha(100) & \beta(100) \\ \dfrac{d\alpha}{dp}(100) & \dfrac{d\beta}{dp}(100) \\ \alpha(130) & \beta(130) \\ \dfrac{d\alpha}{dp}(130) & \dfrac{d\beta}{dp}(130) \end{bmatrix}$$

In the example above, we can see that the time to compute the library is halved for the one dimensional problem when spectral derivatives are available; presuming the cost to produce the spectral derivatives is negligible via the adjoint method.

For multidimensional problems, the formulation is quite similar, with the exception that the monomials will be made up of cross-terms formed from the elements of the parameter vector. For example, for the two dimensional interpolation problem, a cubic multidimensional polynomial derived from parameter $p=[x\ y]^T$ be comprised of ten monomials in x and y. For each parameter value, the system matrix is made up of three-row blocks with ten columns, one for each monomial $$R_A(p) = \begin{bmatrix} 1 & x & y & x^2 & xy & y^2 & x^3 & x^2y & xy^2 & y^3 \\ 0 & 1 & 0 & 2x & y & 0 & 3x^2 & 2xy & y^2 & 0 \\ 0 & 0 & 1 & 0 & x & 2y & 0 & x^2 & 2xy & 3y^2 \end{bmatrix}$$

The associated rows of the matrix B are $$R_B(p) = \begin{bmatrix} \alpha(p) & \beta(p) \\ \dfrac{d\alpha}{dx}(p) & \dfrac{d\beta}{dx}(p) \\ \dfrac{d\alpha}{dy}(p) & \dfrac{d\beta}{dy}(p) \end{bmatrix}$$

In one embodiment of the library interpolation method, local cubic multidimensional models are built on the fly in a region where the solution is expected to lie. Numerical experiments indicate that for a given volume of parameter space, the expected precision of the local models is roughly equal when the library space contains the same number of independent data, whether that data is comprised of just spectra or spectra and derivatives. In other words, for a parameter space with M degrees of freedom, one might expect the same accuracy of the local models for (M+1) N spectra evaluations or N spectral evaluations with MN derivatives. If we presume the time to compute the spectral derivatives is negligible compared to the spectra, then we can expect a speed-up of a factor of M+1 in the time it takes to compute a library.

In the following description, numerous specific details are set forth in order to provide a thorough understanding of embodiments of the present invention. Embodiments of the present invention may be practiced without some or all of these specific details. In other instances, well known process operations have not been described in detail in order not to unnecessarily obscure the present invention.

Spectroscopic Scatterometer

FIG. 1 is a schematic view of a representative spectroscopic scatterometer system, according to an embodiment of the invention. As shown in FIG. 1, a semiconductor wafer 102 may comprise a silicon substrate 102a, a film 102b on the substrate and a diffracting structure 102c such as a photoresist pattern on the film, where the film is at least partially light-transmissive and has a certain film thickness and refractive index (n and k, the real and imaginary components of the index).

Before the diffracting structure 102c is measured, an XYZ stage 104 is used for moving the wafer in the horizontal XY directions in order to first measure the film thickness and refractive index of the underlying structure underneath the photoresist pattern 102c.

For the purpose of measuring the film thickness and refractive index of the underlying structure (102b and 102a), a broadband radiation source such as white light source 106 supplies light through a fiber optic cable 108 which randomizes the polarization and creates a uniform light source for illuminating the wafer. Upon emerging from fiber 108, the radiation passes through an optical illuminator that may include a slit aperture and a focus lens (not shown). The slit aperture causes the emerging light beam to image a small area of layer 102b. The light emerging from illuminator 110 is polarized by a polarizer 112 to produce a polarized sampling beam 114 illuminating the layer 102b.

The radiation originating from sampling beam 114 that is reflected by layer 102b, passed through an analyzer 116 and to a spectrometer 118 to detect different spectral components of the reflected radiation. In the spectroscopic ellipsometry (SE) mode of system 100 for measuring film thickness and refractive index, either the polarizer 112 or the analyzer 116 is rotated (to cause relative rotational motion between the polarizer and the analyzer) when spectrometer 118 is detecting the reflected light at a plurality of wavelengths, such as those in the spectrum of the radiation source 106, where the rotation is controlled by computer 120 in a manner known to those skilled in the art. The reflected intensities at different wavelengths detected is supplied to computer 120 which computes the film thickness and n and k values of the refractive index of layer 102b.

Frequency Domain

Figure 2:
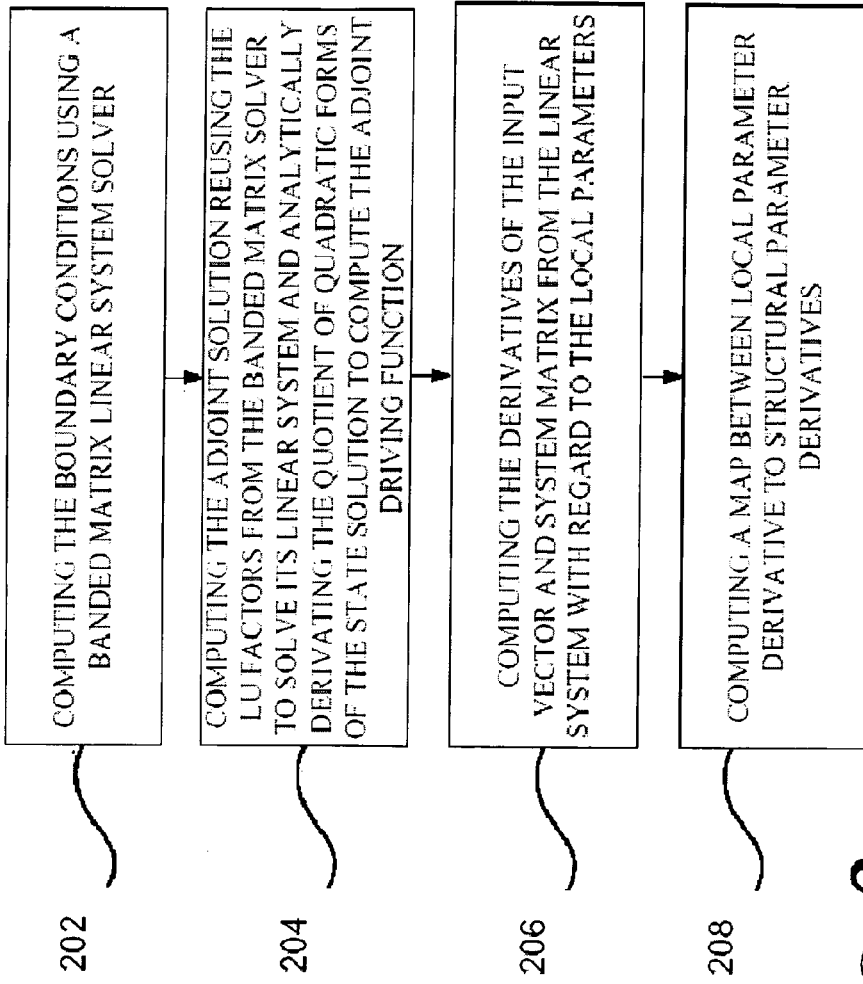
FIG. 2 is a flow diagram of a method with computations in a frequency domain in accordance with an embodiment of the present invention.

As shown in FIG. 2, for the RCWA based adjoint frequency domain embodiment of the present invention, the elements 200, described in more detail below, include the computation of the entire boundary conditions and the reflection and transmission coefficients using a banded or block banded matrix linear system solver (202); and the computation of the adjoint solution reusing matrice from the LU-factorization factors, including pivoting permutations, from the banded or block banded matrix solver to solve its linear system and analytically derivating the quotient of quadratic forms of the state solution to compute the adjoint source function (204). LU factorization refers to the algorithm by which a matrix is factored into the product of lower and upper triangular matrices.

In the embodiment where derivatives with respect to geometric parameter are desired, the computation continues with the computation of the derivatives of the input vector and system matrix from the linear system of step 1 (202) above with regard to the local parameters, such as slab heights and CD fractions (206); the computation of a set of local parameter derivatives, namely with respect to slab heights and CD fractions, computed via the inner product of the state and the adjoint vectors weighted by the derivatives of the state matrix with regard to local parameter derivatives; and the computation of a map between local parameter derivatives (208), and geometric parameter derivatives, such as grating height, width, and sidewall angle.

In the embodiment where derivatives with respect to optical parameters are desired, the computation (204) is followed by the optional computation (206), the computation of the derivatives of the state input vector and system matrix from the linear system of computation (202) above with regard to the optical parameters, and the optional computation of optical parameter derivatives of the inner product between the adjoint and the difference between the derivative of the state input vector and the product of the state and the derivative of the state matrix (from computation 206).

A scattering problem may be described as light impinging on a geometrical structure and measuring the fraction of light that is reflected and/or transmitted. These geometric structures typically include an incident layer, a grating layer with a parameterized geometry, and a substrate layer. While both the incident layer and the substrate layer have uniform index of refractions, the grating layer has a non-uniform index of refraction. This non-uniformity may be viewed as a function of height and length.

An illustration of a scattering problem may include a grating region that contains two rectangular areas with different indices of refraction, $n_a$ and $n_b$. The sum of the widths of the rectangular regions constitute the pitch, $\Lambda$, and the width of the rectangle associated with index of refraction, $n_b$, is the critical dimension (CD). The geometry of this problem may be parameterized by grating height, h, and CD fraction, $f=CD/\Lambda$.

One technique to compute the solution of this scattering problem is to use the RCWA framework, casting the problem as the solution to a linear system, $Ax=b$, where A is the system matrix and b is the system input vector. In the transverse electric (TE) field case, this linear system may be written as $A_e x_e = b_e$ or:

$$\begin{bmatrix} -I & I & e^{-\sqrt{C}\bar{h}} & 0 \\ jY_I & \sqrt{C} & -\sqrt{C}e^{-\sqrt{C}\bar{h}} & 0 \\ 0 & e^{-\sqrt{C}\bar{h}} & I & -I \\ 0 & \sqrt{C}e^{-\sqrt{C}\bar{h}} & -\sqrt{C} & -jY_{II} \end{bmatrix} \begin{bmatrix} r_e \\ c_m^+ \\ c_m^- \\ t_e \end{bmatrix} = \begin{bmatrix} N \\ ja_I N \\ 0 \\ 0 \end{bmatrix}. \quad (1)$$

The constituent elements of the system matrix $A_e$ and the system input vector $b_e$ are defined along the lines of (1) and are given as follows. The matrix $$C = K_x^2 - E, \quad (2)$$

is the difference between the square of the diagonal matrix $K_x$ that contains the weightings of the diffraction modes in the forward (horizontal) direction of the incident light and the matrix E, and a Toeplitz matrix comprised of the difference of the Fourier coefficients of the function describing the permittivity in the grating region. The constant $\bar{h}=k_0 h$ is the height of the grating weighted by the wave number of the incident light. The matrices $Y_I$ and $Y_{II}$ contain the weightings of the diffraction modes in the vertical direction of the incident light in the incident and substrate layer, respectively. The vector N is a vector that indicates the amplitude and order number of the incident electric field. The constant $a_I$ depends on the incident angle and index of refraction.

The solution to the linear system $x_e$ contains sought after values the reflection coefficient, $r_e$, and the transmission coefficient, $t_e$, as well as two coefficients describing the boundary conditions between the grating layer and the incident layer, and the grating layer and the substrate layer.

It should be noted that this simple geometry forms a basis for solving the scattering problems, as they may be built up with many individual slabs having rectangular geometries, in Ziggurat fashion. In this embodiment, the system solution vector is elongated containing additional terms describing the boundary conditions between each slab.

Similarly, the linear system for the transverse magnetic (TM) field case may be written as $A_m x_m = b_m$ or $$\begin{bmatrix} -I & I & e^{-\sqrt{B}\bar{h}} & 0 \\ jZ_I & A\sqrt{B} & -A\sqrt{B}e^{-\sqrt{B}\bar{h}} & 0 \\ 0 & e^{-\sqrt{B}\bar{h}} & I & -I \\ 0 & A\sqrt{B}e^{-\sqrt{B}\bar{h}} & -A\sqrt{B} & -jZ_{II} \end{bmatrix} \begin{bmatrix} r_m \\ b_m^+ \\ b_m^- \\ t_m \end{bmatrix} = \begin{bmatrix} N \\ jb_I N \\ 0 \\ 0 \end{bmatrix} \quad (3)$$

where $$B=A^{-1}(K_x E^{-1} K_x - I), \quad (4)$$

$Z_I, Z_{II}, N$, and $b_I$ are similarly defined in (1). Here, the matrix A is a Toeplitz matrix comprised of the difference of the Fourier coefficients of the function describing the inverse of the permittivity in the grating region.

Inferring the geometry of the scattering region requires finding the parameter values, p, associated with the spectra $\alpha$ and $\beta$, that are closest to measured spectra, $\alpha_0$ and $\beta_0$. The measure of closeness is given by an objective function; this is often a quadratic form based on the differences between measured and computed spectra. In the above example, this would entail finding the grating height, h, and CD fraction, $f$, whose attendant spectra when differenced with the measured spectra minimizes the quadratic form. A suitable objective function, J, used within the RCWA framework may be defined based on functions of the state vectors, $x_e$ and $x_m$:

$$J = \frac{1}{2}(\alpha - \alpha_0)^2 + \frac{1}{2}(\beta - \beta_0)^2 \qquad (5)$$

where $$\alpha = I_\alpha / I_0 \qquad (6)$$

and $$\beta = I_\beta / I_0 \qquad (7)$$

with $$I_0 = x_e^H ss^T x_e + x_m^H cc^T x_m, \qquad (8)$$

$$I_\alpha = x_m^H cc^T x_m - x_e^H ss^T x_e, \qquad (9)$$

$$I_\beta = 2\mathcal{R}(x_e^H sc^T x_m), \qquad (10)$$

The vectors s and c are defined as:

$$s = \sin(\eta) e_{r0} \qquad (11)$$

and $$c = \cos(\eta) e_{r0} \qquad (12)$$

where the vector $e_{r0} = [0 \ldots 0\ 1\ 0 \ldots 0]^T$ Or extracts the zero$^{th}$ order reflection coefficient from the state vectors $x_e$ and $x_m$ in (1) and (2) respectively. The angle $\eta$ is the analyzer angle. The derivatives of the objective function with regard to the parameter vector $p = [f, h]^T$ may be written as follows $$\nabla_p J = \Re\left(\hat{x}_e^H (\nabla_p b_e - \nabla_p(A_e x_e)) + \hat{x}_m^H (\nabla_p b_m - \nabla_p(A_m x_m))\right) \qquad (13)$$

where the adjoint vectors, $\hat{x}_e$ and $\hat{x}_m$, are the solutions of the linear systems $$A_e^H \hat{x}_e = \nabla_{xe}^H J \qquad (14)$$

and $$A_m^H \hat{x}_m = \nabla_{xm}^H J. \qquad (15)$$

In the embodiment described in this section, the spectra of interest is defined as $\alpha$ and $\beta$; however, this definition may be made more general by allowing any function of the state to be considered as spectra. Such functions may be quadratic functions of the state, among whose class Mueller matrix elements belong, or linear functions of the state, among whose class Jones matrix elements belong. Such reformulations would be evident to one of skill in the art.

Matrix Derivatives

The computation of (13) includes the computation of derivatives of scalar functions relative to vectors and matrices relative to scalars. Starting with the right hand sides of (14) and (15):

$$\nabla_{xe} J = (\alpha - \alpha_0) \nabla_{xe} \alpha + (\beta - \beta_0) \nabla_{xe} \beta \qquad (16)$$

where $$\nabla_{xe} \alpha = (I_0 \nabla_{xe} I_\alpha - I_\alpha \nabla_{xe} I_0) / I_0^2 \qquad (17)$$

and $$\nabla_{xe} \beta = (I_0 \nabla_{xe} I_\beta - I_\beta \nabla_{xe} I_0) / I_0^2, \qquad (18)$$

with similar definition for $\nabla_{xm} J$, that is, the derivative of the objective function with respect to $x_m$. The derivatives of $I_0$, $I_\alpha$, and $I_\beta$ with respect to the state vectors, $x_e$ and $x_m$, may be written as follows:

$$\nabla_{xe} I_0 = 2(x_e^H s)s^T,\ \nabla_{xm} I_0 = 2(x_m^H c)c^T \qquad (19)$$

$$\nabla_{xe} I_\alpha = -2(x_e^H s)s^T,\ \nabla_{xm} I_\alpha = 2(x_m^H c)c^T \qquad (20)$$

$$\nabla_{xe} I_\beta = -2(x_m^H c)s^T,\ \nabla_{xm} I_\beta = 2(x_e^H s)c^T. \qquad (21)$$

Next, compute the values of:

$$\nabla_p (A_e x_e) = \left[\left(\frac{\partial A_e}{\partial f}\right) x_e, \left(\frac{\partial A_e}{\partial h}\right) x_e\right] \qquad (22)$$

and $$\nabla_p (A_m x_m) = \left[\left(\frac{\partial A_m}{\partial f}\right) x_m, \left(\frac{\partial A_m}{\partial h}\right) x_m\right]. \qquad (23)$$

In the problem given, the values of $\nabla_p b_e = 0$ and $\nabla_p b_m = 0$; however, this in general is not so, particularly for optical parameters like angle of incidence, pitch, and wavelength.

Note from (2) that the Fourier expansion of the permittivity function $\epsilon(\cdot)$ is given as:

$$\varepsilon_k = \begin{cases} n_b^2 f + n_a^2(1-f); & k = 0 \\ (n_b^2 - n_a^2)\frac{\sin(\pi k f)}{\pi k}; & k \neq 0 \end{cases} \quad (24)$$

The matrix E in (2) and (4) is a Toeplitz matrix formed from the elements of $\epsilon$, i.e., $[E]_{ij} = \epsilon_{i-j}$. Similarly, the Fourier expansion of the prohibitivity function $a = 1/\epsilon$ is given as:

$$a_k = \begin{cases} n_b^{-2} f + n_a^{-2}(1-f); & k = 0 \\ (n_b^{-2} - n_a^{-2})\frac{\sin(\pi k f)}{\pi k}; & k \neq 0. \end{cases} \quad (25)$$

The matrix A in (4) is also a Toeplitz matrix formed from the elements of a, i.e., $[A]_{ij} = a_{i-j}$. Since $\epsilon$ and a are analytic in $f$, they may be differentiated, $$\frac{d\varepsilon_k}{df} = (n_b^2 - n_a^2)\cos(\pi k f); \quad \frac{da_k}{df} = (n_b^{-2} - n_a^{-2})\cos(\pi k f). \quad (26)$$

It should be noted that while in this case the derivative of the Fourier components matrices E and A have been computed analytically, they may also be computed numerically. Since the numerical derivative involves ultimately the derivation of a vector with regard to a scalar (or set of scalars in a plurality of materials in the grating), the numerical computation of the derivatives by finite differences is efficient and does not materially impact the speed of the method.

It should also be noted that the parameterization of the discrete change in permittivity by a single parameter, namely CD fraction, may not be adequate for describing index of refraction in the slab. For example, multiple materials in the slab might require multiple parameters akin to CD fraction. A slab wherein there is a smooth (as opposed to an abrupt) change in permittivity might require a different parameterization, such as one that describes a linear or cubic spline. A smooth change in slab permittivity may also be desirable particularly when multiple slabs are used to represent a complex shape. Such a smooth description might be a means of more accurately representing the overall permittivity of the structure, resulting in better accuracy with fewer Fourier modes or slabs in the approximation.

The definition of $$\frac{dE}{df}$$

and $$\frac{dA}{df},$$

follows as merely the Toeplitz matrices formed from $$\frac{d\varepsilon}{df}$$

and $$\frac{da}{df}$$

vectors. The definitions of $$\frac{dE^{-1}}{df}$$

and $$\frac{dA^{-1}}{df}$$

are given simply as:

$$\frac{dE^{-1}}{df} = -E^{-1}\frac{dE}{df}E^{-1}; \quad \frac{dA^{-1}}{df} = -A^{-1}\frac{dA}{df}A^{-1}. \quad (27)$$

Next, find the derivatives of the block matrices in the system matrices in (1) and (3) with regard to height, h, and CD fraction, $f$. This is made up of Fréchet derivatives with respect to two functions, the matrix square root and the matrix exponential. To compute these derivatives, assume that E and A are semi-simple matrices and use the spectral product method of computing the Fréchet derivative of a function of a matrix [4]. This may be defined as follows. Suppose $$A = X\Lambda X^{-1} \quad (28)$$

where $\Lambda$ is a diagonal matrix with elements $\lambda_i$ and where the analytical function of interest is defined as $F(\cdot)$. Then the Fréchet derivative of the matrix $F(A)$ in the direction V, i.e., $D_V(F(A))$ is given as:

$$D_V(F(A)) = X(\overline{V} \circ \Delta_\lambda(F))X^{-1} \quad (29)$$

with $\circ$ denoting the Hadamard (element by element) product, $\overline{V} = X^{-1}VX$, and $$[\Delta_\lambda(F)]_{ij} = \begin{cases} (F(\lambda_i) - F(\lambda_j))/(\lambda_i - \lambda_j); & \lambda_i \neq \lambda_j \\ F'(\lambda_i); & \lambda_i = \lambda_j \end{cases}. \quad (30)$$

The definition of the Fréchet derivative in (29) provides a particularly efficient mechanism to compute the derivative of the system matrices $A_e$ and $A_m$, as it involves using many of the computational by-products available from the computation of the spectra. In an alternative embodiment, a method for computing the Fréchet derivative of the square root of a matrix is via a Lyapunov equation, that is, if the eigenvector decomposition of the matrix is available, the solution of the Lyapunov equation reduces to the solution of a diagonal system. Also, it should be noted that the methods described herein to compute the Fréchet derivative may be focused on spectral methods. Other methods to compute the Fréchet derivative may be based on functions of block upper triangular matrices with the system matrices on the diagonal and the derivative direction in the upper right hand quadrant.

In the TE case, it is noted that $dC/df = -dE/df$; thus:

$$\frac{d}{df}\sqrt{C} = D_{\frac{dC}{df}}(\sqrt{C}) \tag{31}$$

and $$\frac{\partial}{\partial f}e^{-\sqrt{C}\hbar} = D_{-\hbar\frac{d\sqrt{C}}{df}}(e^{-\sqrt{C}\hbar}). \tag{32}$$

The derivative of the system matrix with respect to CD fraction, $$\frac{\partial A_e}{\partial f},$$

is then given by:

$$\frac{\partial A_e}{\partial f} = \begin{bmatrix} 0 & \frac{\partial e^{-\sqrt{C}\hbar}}{\partial f} & 0 & 0 \\ \frac{d}{df}\sqrt{C} & -\frac{d\sqrt{C}}{df}e^{-\sqrt{C}\hbar} & 0 & 0 \\ & \sqrt{C}\frac{\partial e^{-\sqrt{C}\hbar}}{\partial f} & & \\ \frac{\partial e^{-\sqrt{C}\hbar}}{\partial f} & 0 & 0 & 0 \\ \frac{d\sqrt{C}}{df}e^{-\sqrt{C}\hbar} + & -\frac{d\sqrt{C}}{df} & 0 & 0 \\ \sqrt{C}\frac{\partial e^{-\sqrt{C}\hbar}}{\partial f} & & & \end{bmatrix} \tag{33}$$

Given that $$\frac{dB}{df} = \frac{dA^{-1}}{df}(K_xE^{-1}K_x - I) + A\left(K_x\frac{dE^{-1}}{df}K_x\right),$$

the derivative of the system matrix with respect to CD fraction, $$\frac{\partial A_m}{\partial f},$$

is defined analogously.

The derivatives of the system matrices with regard to the height h may be computed using the derivative of the matrix exponential:

$$\frac{\partial}{\partial h}e^{-\sqrt{C}\hbar} = -k_0\sqrt{C}e^{-\sqrt{C}\hbar}. \tag{34}$$

Thus, the derivative of the system matrix with respect to height, $$\frac{\partial A_e}{\partial h},$$

may be written as:

$$\frac{\partial A_e}{\partial h} = \begin{bmatrix} 0 & -k_0\sqrt{C}e^{-\sqrt{C}\hbar} & 0 & 0 \\ 0 & k_0Ce^{-\sqrt{C}\hbar} & 0 & 0 \\ -k_0\sqrt{C}e^{-\sqrt{C}\hbar} & 0 & 0 & 0 \\ -k_0Ce^{-\sqrt{C}\hbar} & 0 & 0 & 0 \end{bmatrix}, \tag{35}$$

with $$\frac{\partial A_m}{\partial h}$$

given analogously.

It should also be noted the framework discussed in this example represents a two dimensional grating. The extension of this example to three dimensions is evident to one of skill in the art.

Numerical Example

Figure 3:
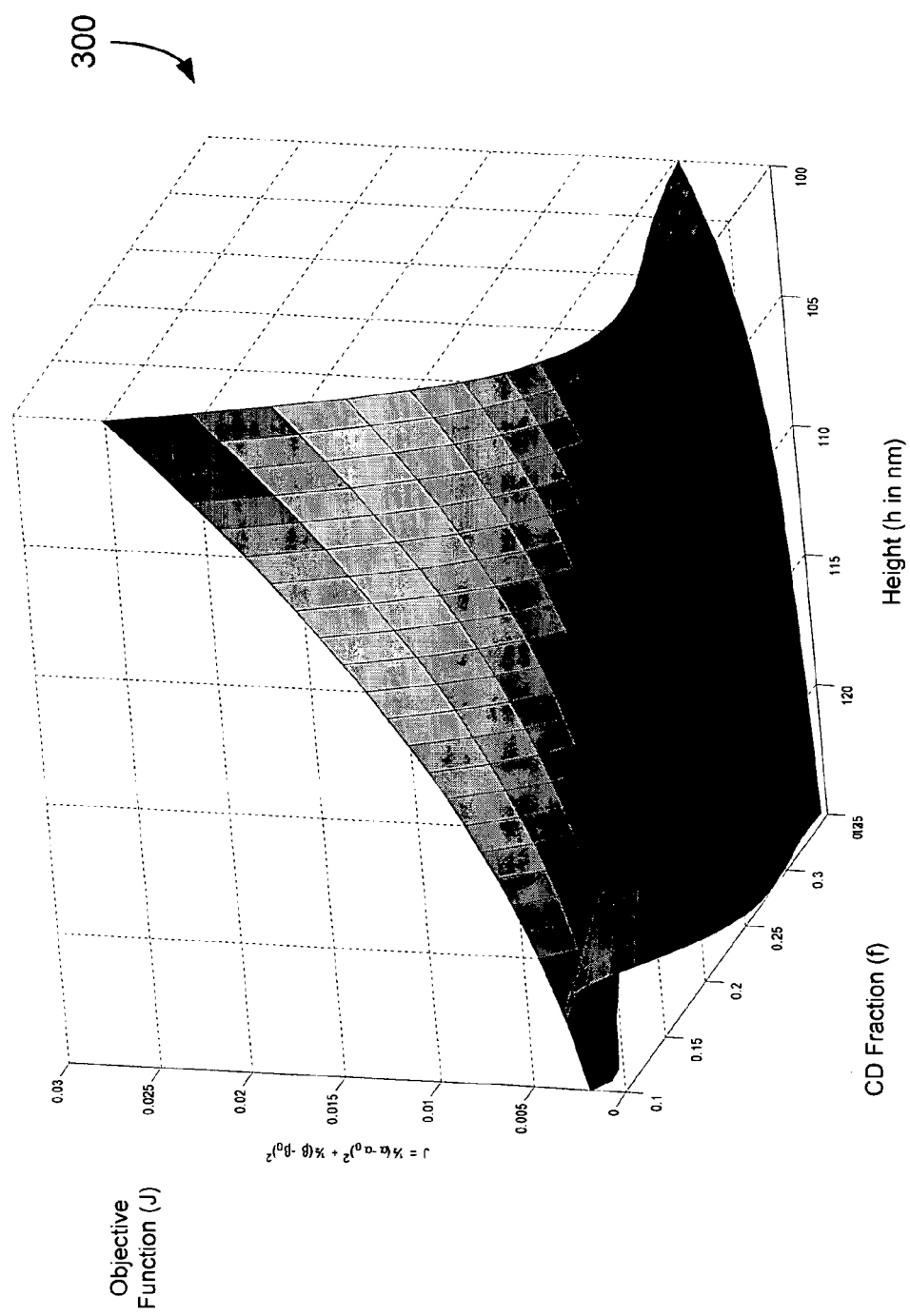
FIG. 3 is a surface plot of the objective function in accordance with an embodiment of the present invention.
Figure 4A:
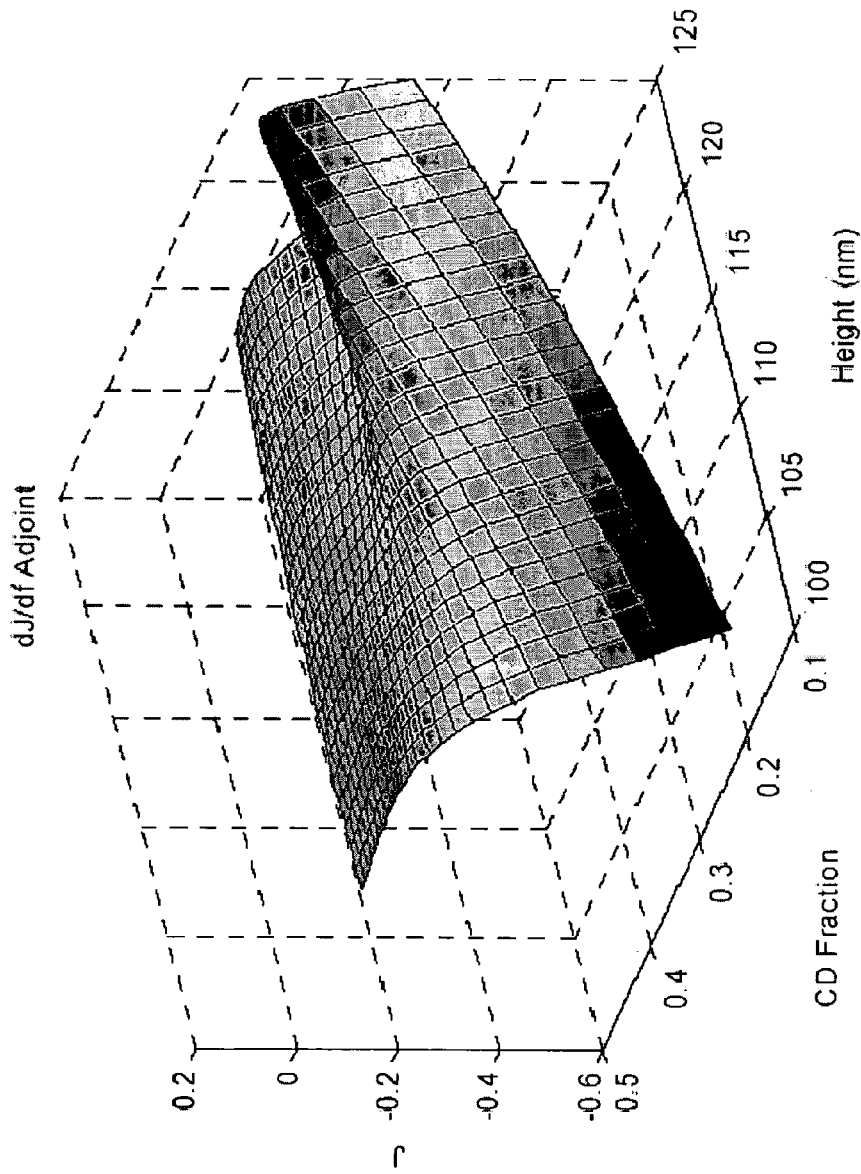
Figure 4B:
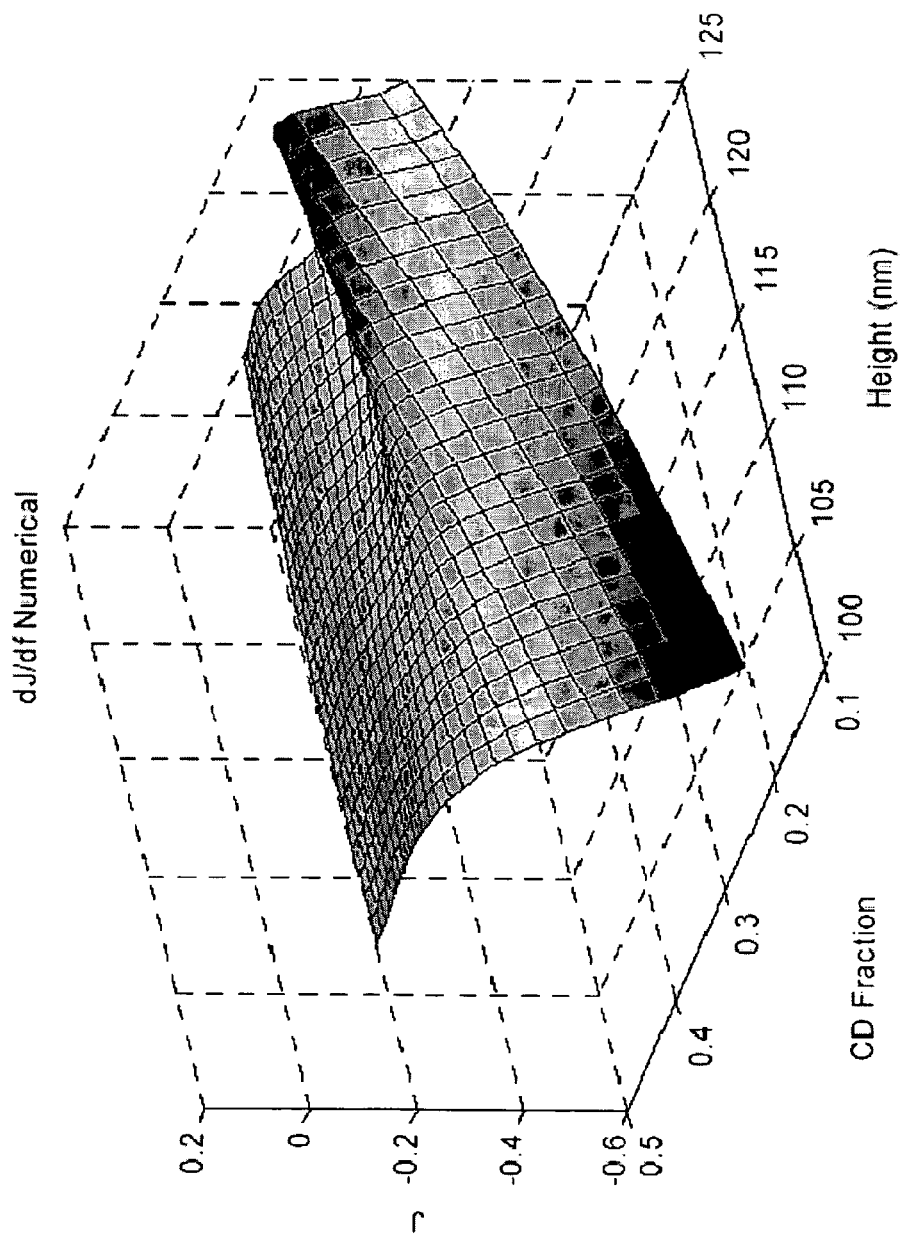
Figure 4D:
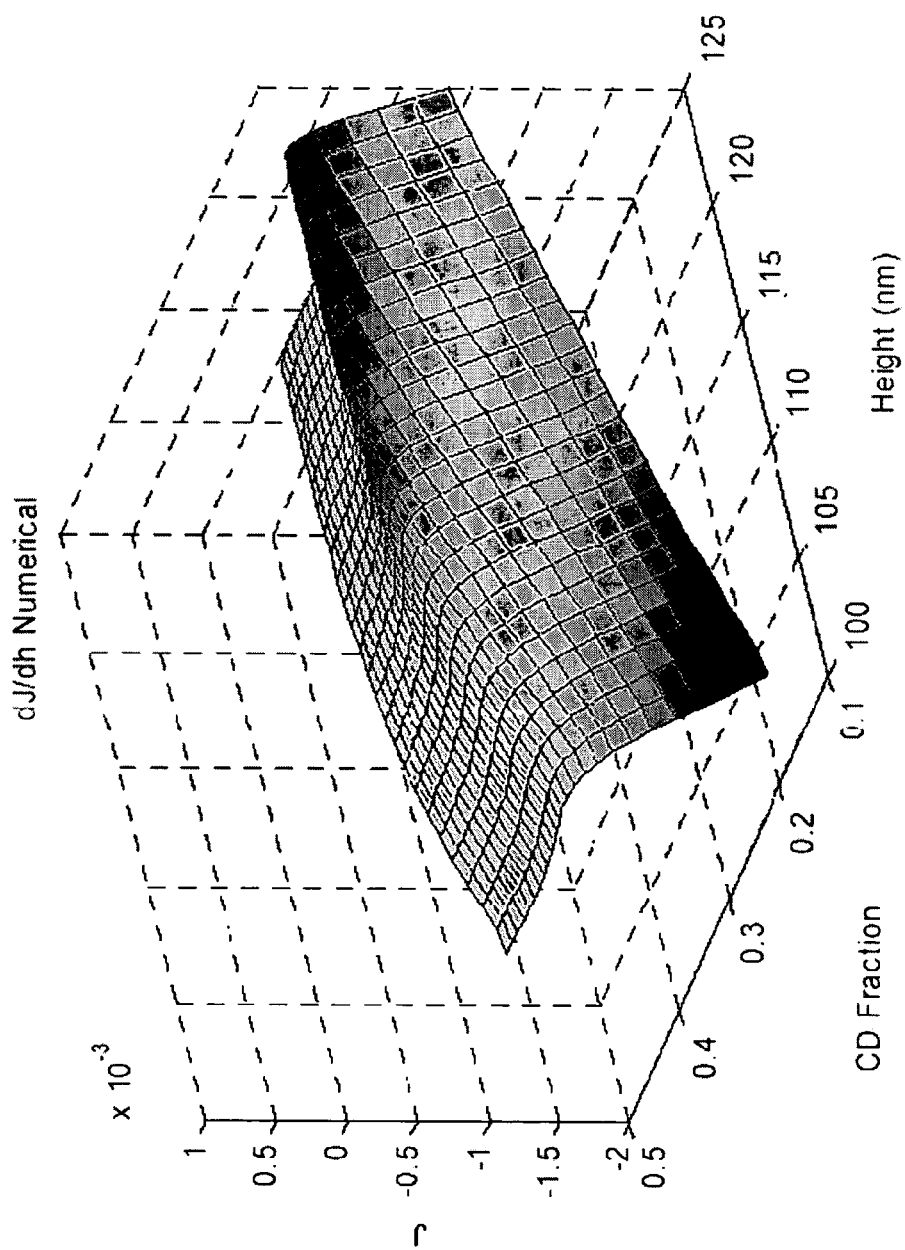

The following example is an illustration of a method of the present invention, but is not meant to be limiting to specifics of the example. The numerical example is given, with indices of refraction $n_f = n_a = 1$ and $n_{ll} = n_b = 2$, impinging light wavelength $\lambda_0 = 350$ nm, pitch $\Lambda = 400$ nm, height $d = 110$ nm, CD fraction $f = 0.25$, and analyzer angle $\phi = -25°$. These values give $\alpha_0 = 0.5795$ and $\beta_0 = -0.8033$. The value of the objective function J may be viewed as a surface 300 over the two parameters, height h, and CD fraction $f$, and is depicted in FIG. 3.

A plot of the derivatives the objective function J with regard to height h and CD fraction $f$ are computed two ways, first with the adjoint method of the present invention, and secondly using finite differences. These values coincide, as is shown in FIGS. 4A, 4B, 4C and 4D.

Figure 5:
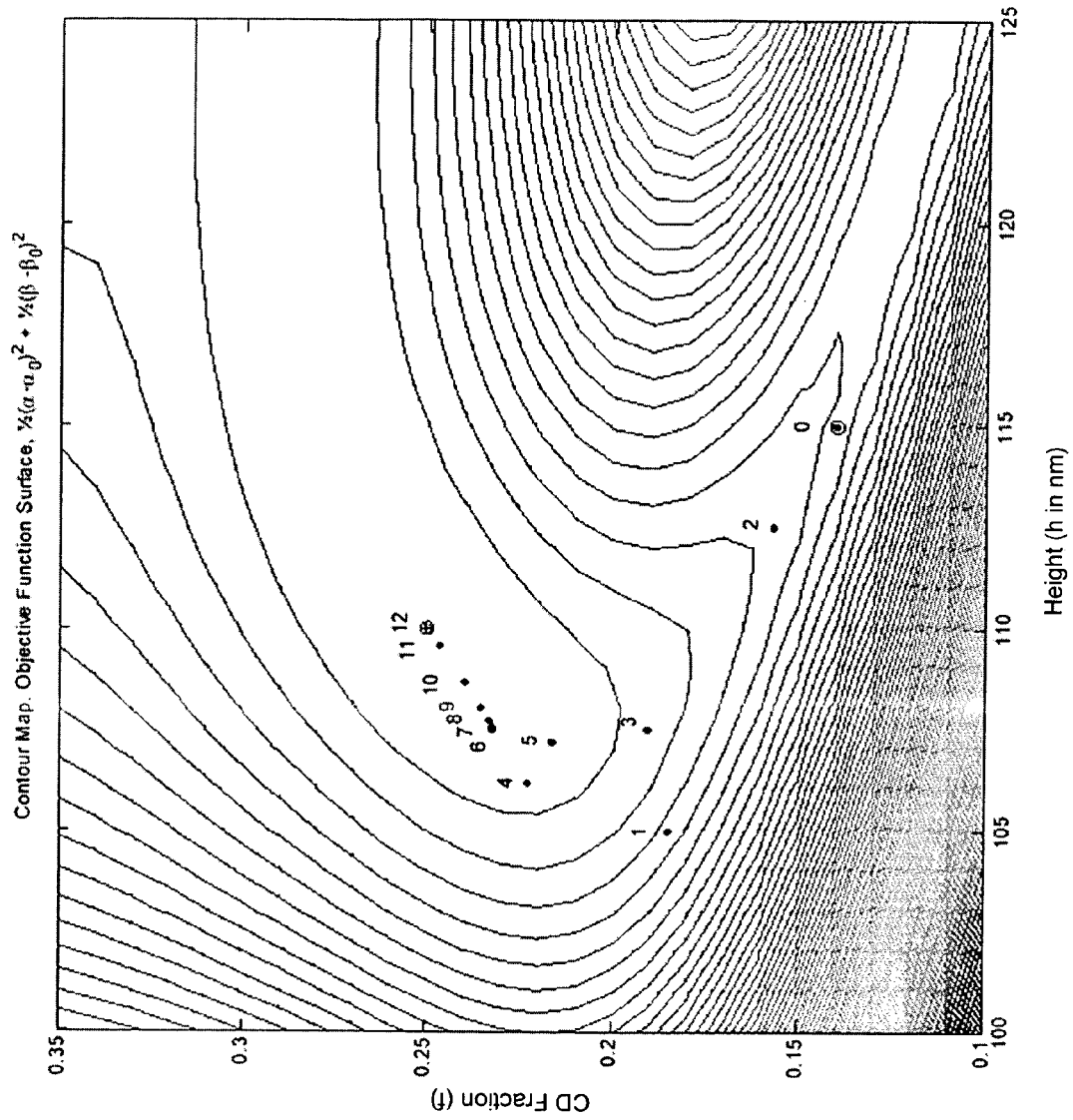
FIG. 5 is the progression of the algorithm plotted on top of a contour plot of the objective function surface regression, according to an embodiment.

In this embodiment, the objective function value and gradient are used in a regression in which the optimization method is a trust-region Newton method. The regression starts with initial value h=115 nm and $f = 0.14$. The optimization routine converges to within 0.1% of correct value h=110 and $f = 0.25$ in 13 iterations. The progression of the algorithm is plotted on top of a contour plot of the objective function surface, and is shown in FIG. 5.

Time Domain

Figure 6:
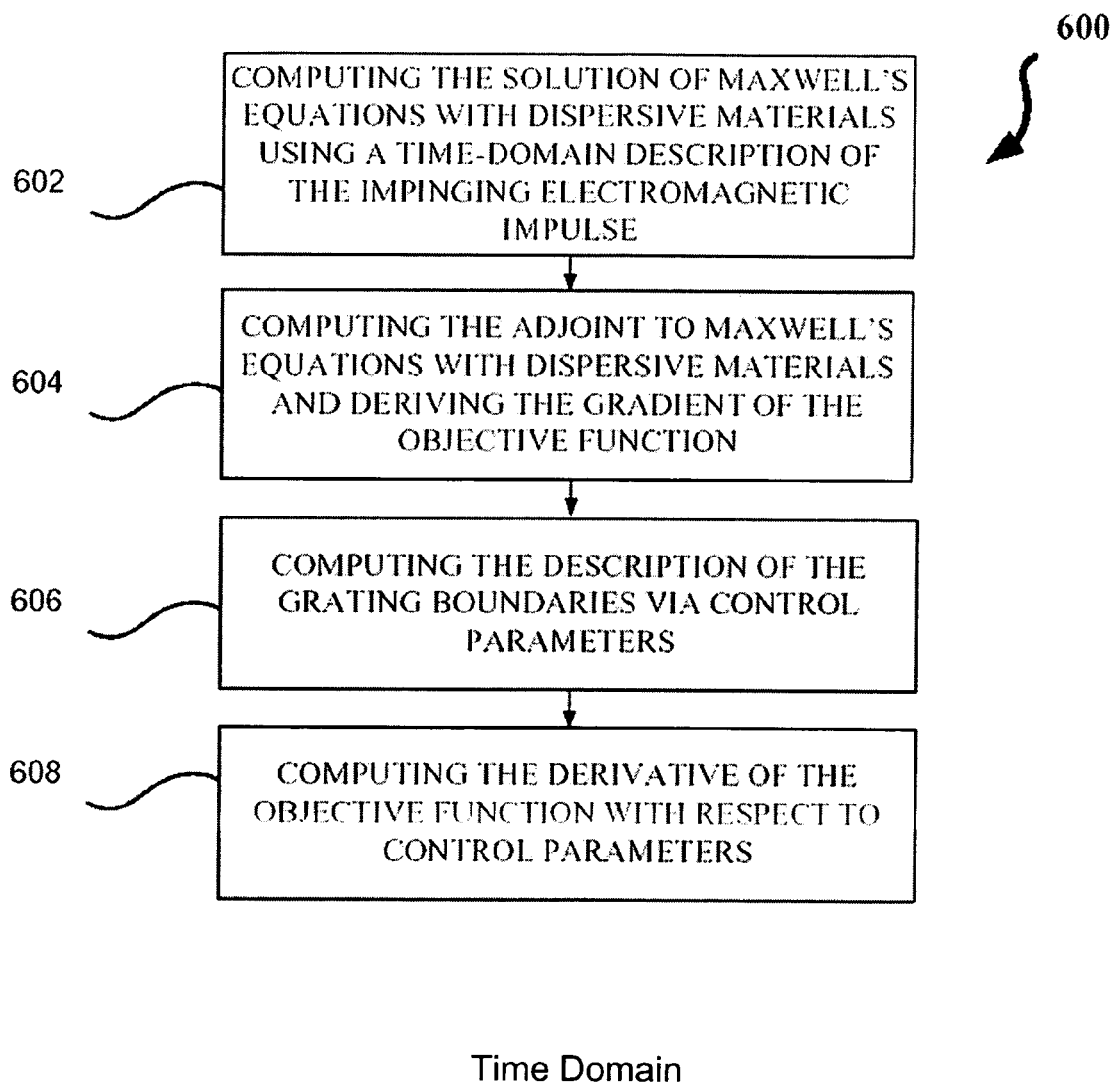
FIG. 6 is a flow diagram of a method with computations in a time domain in accordance with an embodiment of the present invention.

In the time domain embodiment, as illustrated in FIG. 6, the elements 600 of the formulation include: 1) The computation of the solution of Maxwell's equations with dispersive materials (602), which is referred to as the state equation, using a time-domain description of the impinging electromagnetic impulse; 2) the computation of the adjoint to Maxwell's equations with dispersive materials and deriving the gradient of the objective function with respect to the state equation (604) to serve as the source functional of the adjoint equation; 3) the computation of the description of the grating boundaries via control parameters (606); and 4) the computation of the derivative of the objective function with respect to control parameters (608) by computing an inner-product between the state equation and adjoint equation in the appropriate Sobolev space defined by a relation given by control parameters.

In an embodiment including mirror symmetry of the grating relative to the incident light, the computation of the time domain adjoint equation may be replaced by a suitable scaling of the state equations.

In the time domain solution embodiment of the present invention, the reflection coefficients are determined by the Fourier transform of the reflected electromagnetic field $u_r(t)$ divided by the Fourier transform of the incident pulse $u_i(t)$ at an observation point (dependence of $u_r(t)$ on spatial variables has been omitted).

$$T(\omega) = \frac{A_r(\omega)}{A_i(\omega)} \quad (0.1)$$

$$A_r(\omega) = \int_0^T u_r(t)\exp(-i\omega t)\,dt,$$

$$A_i(\omega) = \int_0^T u_i(t)\exp(-i\omega t)\,dt.$$

To solve an inverse equation, find the parameters of grating such that $T(\omega)$ are the same as (or close to) $T^0(\omega)$ for a finite set of $\omega$, $$\{\omega_n\}_{n=1}^N. \quad (0.2)$$

Thus, the inverse equation is a minimization equation. Therefore, q (e.g. geometrical parameters of grating) may be found which provides:

$$F(q) = \int_0^T \Phi(u, q)\,dt \to \min$$

where $$F(q) = \sum_{n=1}^N |T(\omega_n) - T^0(\omega_n)|^2. \quad (0.3)$$

In this embodiment, therefore $$\delta F = 2\mathrm{Re}\left(\sum_{n=1}^N \overline{(T(\omega_n) - T^0(\omega_n))}\delta T(\omega_n)\right).$$

From definition (0.1) we have $$\delta T(\omega) = \frac{\delta A_r(\omega)}{A_i(\omega)}$$

and $$\delta F = 2\mathrm{Re}\left(\sum_{n=1}^N \overline{\frac{T(\omega_n) - T^0(\omega_n)}{A_i(\omega_n)}}\delta A_r(\omega_n)\right)$$

and finally $$\delta F = 2\mathrm{Re}\left(\int_0^T \sum_{n=1}^N c_n \exp(-i\omega_n t)\delta u_r\,dt\right) \quad (0.4)$$

where $$c_n = \overline{\frac{T(\omega_n) - T^0(\omega_n)}{A_i(\omega_n)}}$$

are complex numbers calculated for previous direct solution.

Note that the same result may be obtained with a functional with some filtering of $u_r$. Indeed, consider functional:

$$F = \int_0^T |u_{filt}(t) - u_{filt}^0(t)|^2\,dt \quad (0.5)$$

with $u_{filt}$ defined by following finite Fourier series with $$\tilde{\omega}_k = \frac{2\pi k}{T}, k = -K, \ldots 0, \ldots K \quad (0.6)$$

$$u_{filt}(t) = \sum_{k=-K}^K u_k \exp(i\tilde{\omega}_k t).$$

Then, using $$u_k = \frac{1}{T}\int_0^T u_r(s)\exp(-i\tilde{\omega}_k s)\,ds$$

the following filter presentation may be obtained:

$$u_{filt}(t) = \frac{1}{T}\int_0^T \sum_{k=-K}^K \exp(i\tilde{\omega}_k(t-s))u_r(s)\,ds.$$

Alternatively, a more common embodiment with some weights $\{a_k\}$, $a_k$ is a complex number, thus $$u_{filt}(t) = \sum_{k=-K}^K a_k u_k \exp(i\tilde{\omega}_k t) = \frac{1}{T}\int_0^T \sum_{k=-K}^K a_k \exp(i\tilde{\omega}_k(t-s))u_r(s)\,ds.$$

Therefore, Parseval's identity may be obtained:

$$F = \int_0^T |u_{filt}(t) - u_{filt}^0(t)|^2 \, dt = \sum_{k=-K}^{K} |a_k|^2 |u_k - u_k^0|^2.$$

Note if T is provided such that set $\{\omega_n\}_{n=1}^N$ from (0.2) is a subset of $\{\tilde{\omega}_k\}_{k=-K}^K$ (0.6) (or, at least, is approximated by a subset of (0.6)), and take $$a_k = \frac{1}{\frac{1}{T} A_i(\tilde{\omega}_k)}$$

for this subset, put $a_k=0$ for rest frequencies $\tilde{\omega}_k$ from set (0.6), the same functional as (0.3) may be obtained.

Filter is defined by:

$$f_{filt}(t) = \sum_{n=1}^{N} \frac{\exp(-i\omega_n t)}{A_i(\omega_n)}. \quad (0.7)$$

Functional (0.3) may be satisfactorily used for adjoint equation. The right-hand side of the adjoint equation is given by:

$$F_{RHS} = \overline{\frac{\partial \Phi}{\partial u}} = \sum_{n=1}^{N} \overline{c_n} \exp(i\omega_n t). \quad (0.8)$$

Thus, what is known about $T^0(\omega)$. If one measures $|T^0(\omega)|$, i.e. just amplitude of $T^0(\omega)$, one might use the functional:

$$F_{(q)} = \sum_{n=1}^{N} \left(|T(\omega_n)|^2 - |T^0(\omega_n)|^2\right)^2 \quad (0.9)$$

Then $$\delta F = 2 \sum_{n=1}^{N} \left(|T(\omega_n)|^2 - |T^0(\omega_n)|^2\right) 2 Re(\overline{T(\omega_n)} \delta T(\omega_n))$$

Finally, the derivative in the form (0.4)

$$\delta F = 2 Re \left( \int_0^T \sum_{n=1}^{N} c_n \exp(-i\omega_n t) \delta u_r \, dt \right)$$

where $c_n$ is slightly different $$c_n = c(\omega_n) = 2 \left(|T(\omega_n)|^2 - |T^0(\omega_n)|^2\right) \frac{\overline{T(\omega_n)}}{A_i(\omega_n)}. \quad (0.10)$$

The right-hand side of the adjoint equation is given by (0.8). Note that this observation functional is for a single observation point. In other embodiments, an observation plane maybe incorporated. For 0-order scattering from grating:

$$A_{r0}(\omega) = \int_\Gamma \int_0^T u_r(t) \exp(-i\alpha x - i\omega t) \, dt \, dx.$$

Here $\Gamma$ is a segment of observation plane, $\alpha = \omega \sin \phi / c_0$, $\phi$ is an angle of the incident wave.

For m-order mode scattering from grating yields:

$$A_{rm}(\omega) = \int_\Gamma \int_0^T u_r(t) \exp\left(-i\alpha x - m \frac{2\pi}{\Lambda} x - i\omega t\right) dt \, dx$$

where $\Lambda$ is the grating period. The right-hand side of the adjoint equation in this case has spatial distribution $$\exp\left(i\alpha x + m \frac{2\pi}{\Lambda} x\right)$$

on observation plane. The wave $$\exp\left(i\alpha x + m \frac{2\pi}{\Lambda} x + i\omega t\right)$$

is damped and thus this reflection coefficient depends on choice of observation plane.

Observation Functional, Alpha/Beta Coefficients

Using objective function J defined in equation (5):

$$J = \frac{1}{2}(\alpha - \alpha_0)^2 + \frac{1}{2}(\beta - \beta_0)^2 \quad (0.11)$$

Or, alternatively:

$$J = \sum_{n=1}^{N} \frac{1}{2}(\alpha(\omega_n) - \alpha_0(\omega_n))^2 + \frac{1}{2}(\beta(\omega_n) - \beta_0(\omega_n))^2 \quad (0.12)$$

where $\alpha(\omega)$, $\beta(\omega)$ may be expressed by means of bilinear form of coefficients of Jones matrix. The Jones matrix relates TM- and TE-polarized components of the scattered field with TM- and TE-polarized components of incident field.

For a diagonal Jones matrix:

$$r_{pp}(\omega) = T_{TE}(\omega)$$

$$r_{ss}(\omega) = T_{TM}(\omega)$$

$$R_p = |r_{pp}|^2 \quad R_s = |r_{ss}|^2 \quad C_d = Re(r_{pp} r_{ss}^*)$$

where $\alpha(\omega)$, $\beta(\omega)$ are defined by $$\alpha = \frac{R_p\cos^2 A - R_s\sin^2 A}{R_p\cos^2 A + R_s\sin^2 A}, \beta = \frac{C_d\sin(2A)}{R_p\cos^2 A + R_s\sin^2 A} \quad (0.13)$$

and for more complicated full Jones matrix $$\alpha = \frac{M_{01} + M_{11}\cos(2A) - M_{21}\sin(2A)}{M_{00} + M_{10}\cos(2A) - M_{20}\sin(2A)}, \quad (0.14)$$

$$\beta = -\frac{M_{02} + M_{12}\cos(2A) - M_{22}\sin(2A)}{M_{00} + M_{10}\cos(2A) - M_{20}\sin(2A)}$$

where A is analyzer angle and Mueller coefficients are defined by $$M_{00} = \frac{1}{2}(|r_{pp}|^2 + |r_{ps}|^2 + |r_{sp}|^2 + |r_{ss}|^2),$$

$$\ldots, M_{22} = Re(r_{pp}r_{ss}^* + r_{ps}r_{sp}^*)$$

For both embodiments, derivatives of bilinear expressions with respect to TM- and TE-polarized component of field are calculated.

Here, let $E_{TE}$-solution with x-polarized incident field and $E_{TM}$ respectively for y-polarized incident field. Then:

$$r_{pp}(\omega) = \frac{A_{rTE}^x(\omega)}{A_{iTE}^x(\omega)}$$

$$r_{ps}(\omega) = \frac{A_{rTM}^x(\omega)}{A_{iTM}^y(\omega)}$$

$$r_{sp}(\omega) = \frac{A_{rTE}^y(\omega)}{A_{iTE}^x(\omega)}$$

$$r_{ss}(\omega) = \frac{A_{rTM}^y(\omega)}{A_{iTM}^y(\omega)}$$

where $$A_{rTE}^x(\omega) = \int_\Gamma^T \int_0^T E_{rTE}^x(t)\exp(-i\omega t)dt\,dy,$$

$$A_{iTE}^x(\omega) = \int_\Gamma^T \int_0^T E_{iTE}^x(t)\exp(-i\omega t)dt\,dy \text{ and etc.}$$

The derivatives with respect to $E_{rTE}^x$, and the like of quadratic forms $R_p$, $R_s$ may be expressed the same way as for ordinary reflection coefficients. Consider derivative of $C_d$.

Electromagnetic field is a real-valued vector in this context, thus complex conjunction of $r_{ss}$ leads to changing of sign of $\omega$ $$r_{ss}^*(\omega) = r_{ss}(-\omega)$$

and $$C_d(\omega) = Re(r_{pp}(\omega)r_{ss}^*(\omega)) = r_{pp}(\omega)r_{ss}(-\omega) + r_{pp}(-\omega)r_{ss}(\omega).$$

This form is bilinear and may be differentiated as:

$$\delta C_d(\omega) =$$
$$\delta r_{pp}(\omega)r_{ss}(-\omega) + \delta r_{pp}(-\omega)r_{ss}(\omega) + r_{pp}(\omega)\delta r_{ss}(-\omega) + r_{pp}(-\omega)\delta r_{ss}(\omega)$$

$$\delta r_{pp}(\omega) = \delta T_{TE}^x(\omega) = \frac{\delta A_{rTE}^x(\omega)}{A_{iTE}^x(\omega)} = \frac{1}{A_{iTE}^x(\omega)}\int_\Gamma^T \int_0^T \delta E_{rTE}^x(t)\exp(-i\omega t)dt\,dy.$$

Thus, the derivatives of J with respect to $E_{rTE}^x$, $E_{rTE}^y$ and $E_{rTM}^x$, $E_{rTM}^y$ may be calculated and it provides the right hand side of two adjoint equations for TM and TE embodiments, respectively.

Anti-Hermitian Hamiltonian Form of Equations, General

Consider a Maxwell's equation system with the dispersion law $$\frac{\partial \vec{D}}{\partial t} = \nabla \times \vec{H} + F_1 \quad (0.15)$$

$$\frac{\partial \vec{H}}{\partial t} = -\nabla \times \vec{E} + F_2$$

$$\vec{D} = \varepsilon_0\varepsilon_\infty\vec{E} + \varepsilon_0\vec{P},$$

$$P = \sum_{p=1}^P P_p,$$

$$P_p(t) = \int_0^\infty \vec{E}(t-s)\chi_p(s)ds.$$

where $\chi_p$ is a Lorentz susceptibility function $$\chi_p(t) = a_p(e^{b_p t} - e^{\overline{b_p}t})/2, \quad (0.16)$$

$$a_p = -i\gamma_p,$$

$$b_p = -\alpha_p + i\beta_p.$$

Coefficients $\alpha_p$, $\beta_p$ and $\gamma_p$ are parameters of the frequency-domain susceptibility function:

$$\chi_p(\omega) = (\varepsilon_s - \varepsilon_\infty)\frac{G_p\omega_p^2}{\omega_p^2 + 2i\alpha_p\omega - \omega^2}, \quad (0.17)$$

$$\beta_p = \sqrt{\omega_p^2 - \alpha_p^2},$$

$$\gamma_p = (\varepsilon_s - \varepsilon_\infty)\frac{G_p\omega_p^2}{\beta_p}.$$

The medium polarization $P_p$ is described by the second-order differential equation $$\ddot{P}_p + 2\alpha_p \dot{P}_p + \omega_p^2 P_p = \gamma_p \beta_p E$$

Thus, additional equations are added with $P_p$ and $\dot{P}_p$ and by obtaining Hamiltonian form of Maxwell's equation with Lorentz polarization in ADE form:

$$\varepsilon_0 \varepsilon_\infty \frac{\partial E}{\partial t} = \nabla \times \vec{H} - \varepsilon_0 \sum_p \dot{P}_p + F_1 \quad (0.18)$$

$$\frac{\partial H}{\partial t} = -\nabla \times E + F_2$$

$$\frac{\partial P_p}{\partial t} = \dot{P}_p$$

$$\frac{\partial \dot{P}_p}{\partial t} = \gamma_p \beta_p E - \omega_p^2 P_p - 2\alpha_p \dot{P}_p$$

In order to obtain anti-Hermitian Hamiltonian, variable transformation may be used:

$$\varepsilon E_{old} = E_{new}, \quad (0.19)$$

$$\varepsilon = \varepsilon_0 \varepsilon_\infty$$

$$P_p = \sqrt{\frac{\gamma_p \beta_p}{\varepsilon_0}} \frac{1}{\omega_p} Q_1$$

$$\dot{P}_p = \sqrt{\frac{\gamma_p \beta_p}{\varepsilon_0}} Q_2$$

and rewrite the system in the form $$\frac{\partial E}{\partial t} = \nabla \times \vec{H} - \sum_p \sqrt{\gamma_p \beta_p \varepsilon_0} \, Q_{1p} + F_1 \quad (0.20)$$

$$\frac{\partial H}{\partial t} = -\nabla \times \frac{1}{\varepsilon} E + F_2$$

$$\frac{\partial Q_{1p}}{\partial t} = \omega_p Q_{2p}$$

$$\frac{\partial Q_{2p}}{\partial t} = \sqrt{\gamma_p \beta_p \varepsilon_0} \frac{1}{\varepsilon} E - \omega_p Q_{1p} - 2\alpha_p Q_{2p}.$$

Consider Hamiltonian $\mathcal{H}$:

$$H = \begin{pmatrix} 0 & \nabla \times & 0 & -\sqrt{\gamma_p \beta_p \varepsilon_0} \\ -\nabla \times \frac{1}{\varepsilon} & 0 & 0 & 0 \\ 0 & 0 & 0 & \omega_p \\ \sqrt{\gamma_p \beta_p \varepsilon_0} \frac{1}{\varepsilon} & 0 & -\omega_p & -2\alpha_p \end{pmatrix}. \quad (0.21)$$

Define scalar product with multiplying components E by $\varepsilon^{-1}$. For media with damping coefficient $\alpha_p = 0$ Hamiltonian $\mathcal{H}$ is anti-Hermitian for this scalar product. Spatial differential part of $\mathcal{H}$ changes sign and polarization part of $\mathcal{H}$ is the transposed matrix.

The adjoint operator to $$\frac{\partial}{\partial t} - H \text{ is } -\frac{\partial}{\partial t} - H^*$$

where H* is the transposed complex conjugate matrix to H. Here, adjunction is accomplished in space with scalar product with $\epsilon^{-1}$ and with boundary conditions for all corresponding vectors. Additional concerns regarding boundary conditions and right-hand side (RHS) are considered later. The adjoint equation has the form:

$$-\frac{\partial Y}{\partial t} + H_\alpha Y = F, \quad (0.1)$$

$$Y(T) = 0.$$

where $H_\alpha = -H^*$. Equation (0.22) may be solved in inverse time direction.

Consider $\mathcal{H}_\alpha$. If $\alpha_p = 0$ then $\mathcal{H}_\alpha = \mathcal{H}$ and the adjoint operator is $$-\frac{\partial}{\partial t} + \mathcal{H},$$

else if the $\alpha_p > 0$ the difference is only in sign of the bottom right corner of matrix $\mathcal{H}$ ($2\alpha_p$ instead of $-2\alpha_p$).

By changing variables and unknown functions:

$$\tilde{t} = T - t, \quad (0.23)$$

$$\tilde{Y}_{Ex}(\tilde{t}) = Y_{Ex}(t) \text{ and the same for } Y_{Ey}, Y_{Ez}, Y_{Q1x}, Y_{Q1y}, Y_{Q1z},$$

$$\tilde{Y}_{Hx}(\tilde{t}) = -Y_{Hx}(t) \text{ and the same for } Y_{Hy}, Y_{Hz}, Y_{Q2x}, Y_{Q2y}, Y_{Q2z}.$$

Thus, $$\frac{\partial \tilde{Y}_{Ex}}{\partial \tilde{t}} = -\frac{\partial T_{Ex}}{\partial t} \text{ and the same for } Y_{Ey}, Y_{Ez}, Y_{Q1x}, Y_{Q1y}, Y_{Q1z}$$

$$\frac{\partial \tilde{Y}_{Hx}}{\partial \tilde{t}} = -\frac{\partial T_{Hx}}{\partial t} \text{ and the same for } Y_{Hy}, Y_{Hz}, Y_{Q2x}, Y_{Q2y}, Y_{Q2z}.$$

The last term in $Y_{Q2}$-equations changes sign. Thus, when passing from inverse-time equation to a direct time from $\mathcal{H}_\alpha$ to $\mathcal{H}$ is passed. Finally, the adjoint equation, is the same equation as the direct equation for E, H, $Q_1$, $Q_2$. The only difference being the RHS $$\frac{\partial \tilde{Y}}{\partial \tilde{t}} - \mathcal{H}\tilde{Y} = \tilde{F}, \quad (0.24)$$

$$\tilde{Y}(0) = 0.$$

Mirror Symmetry

Consider incident wave in form:

$$\exp(i\alpha x - i\beta z + i\omega t). \quad (0.25)$$

The observation functional depends on 0-order scattering from grating and is defined by:

$$F(q) = \int_\Gamma \int_0^T \Phi(q, u_r(t,q)) dt dx = \sum_{n=1}^N \left(|T(\omega_n)|^2 - |T^0(\omega_n)|^2\right)^2$$

where $$T(\omega) = \frac{A_r(\omega)}{A_i(\omega)}$$

$$A_r(\omega) = \int_\Gamma \int_0^T u_r(t) \exp(-i\alpha x - i\omega t) \, dt dx \quad (0.2)$$

$$A_i(\omega) = \int_\Gamma \int_0^T u_i(t) \exp(-i\alpha x - i\omega t) \, dt dx$$

where $\Gamma$ is an observation plane, $\alpha = \omega \sin\phi/c_0$, $\phi$ is an angle of the incident wave. The RHS of adjoint system is defined by complex-conjugate derivative of density of observation function $$-\left(\frac{\partial \Phi}{\partial u}\right)^*.$$

Thus, $$F_{RHS} = -\sum_{n=1}^N \overline{c_n} \exp(i\alpha x + i\omega_n t) \text{ for } x \in \Gamma$$

where $$c_n = 2\left(|T(\omega_n)|^2 - |T^0(\omega_n)|^2\right) \frac{\overline{T(\omega_n)}}{A_i(\omega_n)}. \quad (0.3)$$

In variables with "tilde" $\tilde{t} = T - t$, $\tilde{Y}$ $$\tilde{F}_{RHS} = -\sum_{n=1}^N \overline{c_n} \exp(i\alpha x - i\omega_n \tilde{t} + i\omega_n T).$$

Thus, $F_{RHS}$ has the angle of incidence $-\phi$.

Consider the case of profiles with mirror symmetry $f(x) = f(-x)$. By changing variables $$\tilde{x} = -x, \quad (0.28)$$

$\tilde{Y}_{Ex}(\tilde{x}) = -Y_{Ex}(x)$ and the same for $Y_{Hx}$, $Y_{Q1x}$, $Y_{Q1x}$, $\tilde{Y}_{Ey}(\tilde{x}) = -Y_{Ey}(x)$ and for all other components.

Thus, $(\tilde{\nabla} \times \tilde{Y}_E)_x (\nabla \times Y_E)_x$ and the same for $(\tilde{\nabla} \times \tilde{Y}_H)_x$, $(\tilde{\nabla} \times \tilde{Y}_E)_y = -(\nabla \times Y_E)_y$ and for all other components, and equation formulation $$\frac{\partial \tilde{Y}}{\partial \tilde{t}} - \mathcal{H}\tilde{Y} = \tilde{F}_{RHS}, \quad (0.29)$$

$$\tilde{Y}(0) = 0.$$

This is the same equation as (0.24). The right-hand side (RHS) has form $$\tilde{F}_{RHS} = -\sum_{n=1}^N \overline{c_n} \exp(-i\alpha \tilde{x} - i\omega_n \tilde{t} - i\omega_n \tilde{t} + i\omega_n T)$$

Thus, the right-hand side (RHS) has the same angle $\phi$ of incidence as (0.25).

Taking the incident wave in the form:

$$\sin(\alpha x - \beta z + \omega t) \quad (0.30)$$

and making a change in the definition (0.26) exp to sin, real-valued functions without complex-conjugate operation may be computed. The RHS function is in the form $$\tilde{F}_{RHS} = -\sum_{n=1}^N c_n \sin(i\alpha \tilde{x} + i\omega_n \tilde{t} - i\omega_n T).$$

If the observation functional depends only on 0-order scattering from grating the adjoint equation may be computed by the following: 1) Use forward time solution to obtain frequency response of system (frequency response of adjoint system is identical due to mirror symmetry); 2) apply frequency response to RHS of adjoint system; and 3) make inverse Fast Fourier Transform (FFT) of 2) to obtain the time-series response of adjoint system (needed to estimate gradients of observation functional).

Boundary Condition.

To conjugate the differential part of Hamiltonian (0.21) boundary conditions are applied. Let the geometry of the equation be $\Lambda$-periodic with respect to x and unbounded in z direction.

Making conjugation to $$\frac{\partial}{\partial x}$$

$$\int_{x_0}^{x_0+\Lambda} \frac{\partial E_z}{\partial x} \overline{Y} dx = E_z \overline{Y} \Big|_{x_0}^{x_0+\Lambda} - \int_{x_0}^{x_0+\Lambda} E_z \frac{\partial \overline{Y}}{\partial x} dx.$$

Boundary conditions to adjoint variable Y may be obtained from equality $$E_z Y^* \big|_{x_0}^{x_0+\Lambda} = 0. \quad (0.31)$$

In the frequency domain the condition $$E_z(x+\Lambda,\omega)\exp(-ik_x\Lambda)=E_z(x,\omega) \quad (0.32)$$

exists and from (0.31):

$$Y(x+\Lambda,\omega)\exp(-ik_x\Lambda)=Y(x,\omega)$$

In the embodiment including mirror symmetry a change of variables is made: $\tilde{x}=-x$, $\tilde{t}=T-t$. Thus, formally the condition changes to $$\tilde{Y}(\tilde{x}+\Lambda,\omega)\exp(ik_x\Lambda)=\tilde{Y}(\tilde{x},\omega).$$

A complex-adjoint function $\tilde{Y}(\omega)^*$ may be taken with condition (0.32). Because of the real-valued solution of the original equation both frequencies $\omega$ and $-\omega$ are available, which are related by $\tilde{Y}(-\omega)=\tilde{Y}(\omega)^*$. Thus the condition of periodicity remains the same for the adjoint solution.

In order to consider the z-direction, the originally unbounded domain from $-\infty$ to $\infty$ is used and set such that all functions vanish in both directions. Therefore, the same boundary conditions may be used for the adjoint equation.

Observation Functional Gradients

In another embodiment, consider formulation of the adjoint solution based on:

$$\begin{cases} \dfrac{\partial X}{\partial t} - \mathcal{H}X = 0, \\ X(0) = X_0 \end{cases} \quad (0.33)$$

and the observation functional reads as follows:

$$F(q) \equiv \int_0^T \Phi(X, q)\, dt.$$

Variation of (0.33) yields:

$$\begin{cases} \left(\dfrac{\partial L}{\partial q}\delta q\right)X + L\delta X = 0, \\ \delta X(0) = 0, \end{cases}$$

and the observation functional variation is estimated by $$\delta F = \int_0^T \left(\dfrac{\partial \Phi}{\partial q}\delta q + \dfrac{\partial \Phi}{\partial X}\delta X\right) dt$$

The adjoint equation is $$\begin{cases} -\dfrac{\partial Y}{\partial t} - \mathcal{H}^*Y = \dfrac{\overline{\partial \Phi}}{\partial X}, \\ Y(T) = 0. \end{cases} \quad (0.34)$$

Functional variation may be obtained in the form:

$$\delta F = \int_0^T \left(\dfrac{\partial \Phi}{\partial q}\delta q + \left(\left(\dfrac{\partial L}{\partial q}\delta q\right)X, Y\right)\right) dt. \quad (0.35)$$

Formula (0.35) yields a gradient of the functional. Evidently, to calculate the functional, the direct and adjoint solutions in the non-zero region of operator $$\dfrac{\partial L}{\partial q}\delta q$$

is known, for example, to calculate the right-hand side (RHS) of the adjoint equation $c(\omega_n)$, which is a function of a direct solution, is known.

Now looking at the frequency domain formulation in order to optimize our time domain formulation, for each prescribed frequency $\omega_n$ from some finite set $\{\omega_n\}_{n=1}^N$ a pair of direct and adjoint equation is provided as $$\begin{cases} L_\omega X_\omega = 0, \\ T_\omega X_\omega = T_\omega X_\omega^i, \end{cases} \begin{cases} L_\omega^* Y_\omega = f_\omega, \\ T_\omega^* Y_\omega = 0, \end{cases} \quad (0.36)$$

where $T_\omega$ is the boundary operator at the top boundary far from domain of interest, $X_\omega^i$ is the incident wave, and $f_\omega$ is the delta-function of observation plane with coefficient $\overline{c(\omega)}$. This RHS of adjoint equation gives the incident wave in air under the observation plane and so the adjoint equation may be formulated with boundary conditions, which make the direct and the adjoint equations identical. The top boundary condition (TBC) may be substituted by TBC on some "near" boundary. The observation plane in this embodiment is out of the computational domain, but it is optimal because the solution in air may be calculated analytically.

The observation functional variation may be written in the form:

$$\delta F = \sum_{\omega \in \{\omega_n\}} \delta F_\omega = \sum_{\omega \in \{\omega_n\}} (\delta L_\omega X_\omega, Y_\omega). \quad (0.37)$$

In this embodiment, to solve the direct frequency an artificial time domain calculation is made with smooth incident pulse $X_0$. Then Fourier components are extracted and scaling is done in order to obtain $\{X_\omega\}$ for each $\omega \in \{\omega_n\}_{n=1}^N$ (this set prescribes parameters of incident pulse). Doing the same for the adjoint frequency equation, provides $\{Y_\omega\}$ for $\omega \in \{\omega_n\}_{n=1}^N$. Solving the time domain equation with some pulse, then using the Fourier transformation and scaling by $\overline{c(\omega_n)}$. In the embodiment, having mirror symmetry and 0-order observation functional, the adjoint equation is the same as the direct so only scaling is needed.

Thus, the functional variation (0.35) and the time domain adjoint equation (0.34) with RHS from 0 to T are not needed, instead the functional (0.37) and artificial adjoint equation with short pulse are used for the direct equation.

Model-Based Metrology Using Objective Function

Figure 7:
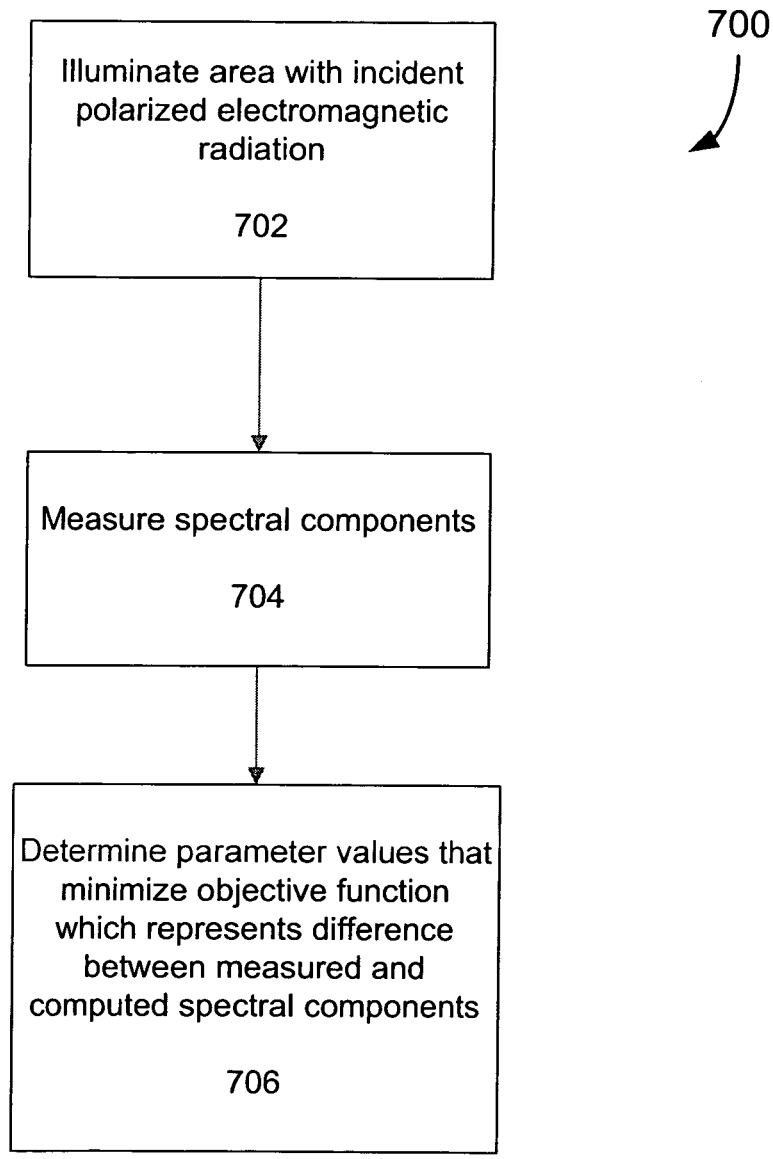
FIG. 7 is a flow chart of a method of model-based metrology in accordance with an embodiment of the invention.

FIG. 7 is a flow chart of a method 700 of model-based metrology in accordance with an embodiment of the invention. An area of a geometrical structure of dispersive materials is illuminated (702) with incident electromagnetic radiation, wherein the incident electromagnetic radiation is polarized, and spectral components of the incident electromagnetic radiation reflected from the area are measured (704). A determination (706) is made as to parameter values that minimize an objective function which represents a difference between the measured spectral components and computed spectral components based on a parameterized model of the geometrical structure.

As disclosed herein, an adjoint-based technique may be advantageously used in determining the parameter values that minimize the objective function. Specific embodiments of this technique are discussed above in relation to FIG. 2 (in the frequency domain) and FIG. 6 (in the time domain).

The steps for determining the parameter values that minimize the objective function may include computing a solution to state equations driven by a function representing the incident electromagnetic radiation, wherein the state equations are derived from Maxwell's equations with dispersive materials, and computing a solution to an adjoint to the state equations.

In one implementation, computing the solution to the state equations may be performed in the frequency domain using a banded matrix linear system solver. Advantageously, the solution to the adjoint to the state equations may then be computed by re-using LU-decomposition factors from the banded matrix linear system solver. In addition, derivatives of the state equations with respect to local parameters may be computed, and a mapping may be computed between derivatives of the state equations with respect to the local parameters and derivatives of the state equations with respect to the geometric parameters.

In another implementation, computing the solution to the state equations may be performed in the time domain. In such an implementation, the technique may compute a description of grating boundaries via control parameters. The technique may also compute a derivative of the objective function with respect to the control parameters, wherein the computation involves computing an inner product between the state and adjoint equations.

The technique disclosed herein may be applied to a grating layer patterned along one direction. For example, such a grating layer may comprise lines of gates for transistors being fabricated.

The technique disclosed herein may be extended by one of skill in the art and applied to a grating layer patterned in two dimensions. For example, such a grating layer may comprise cells for flash memory being fabricated.

Figure 8:
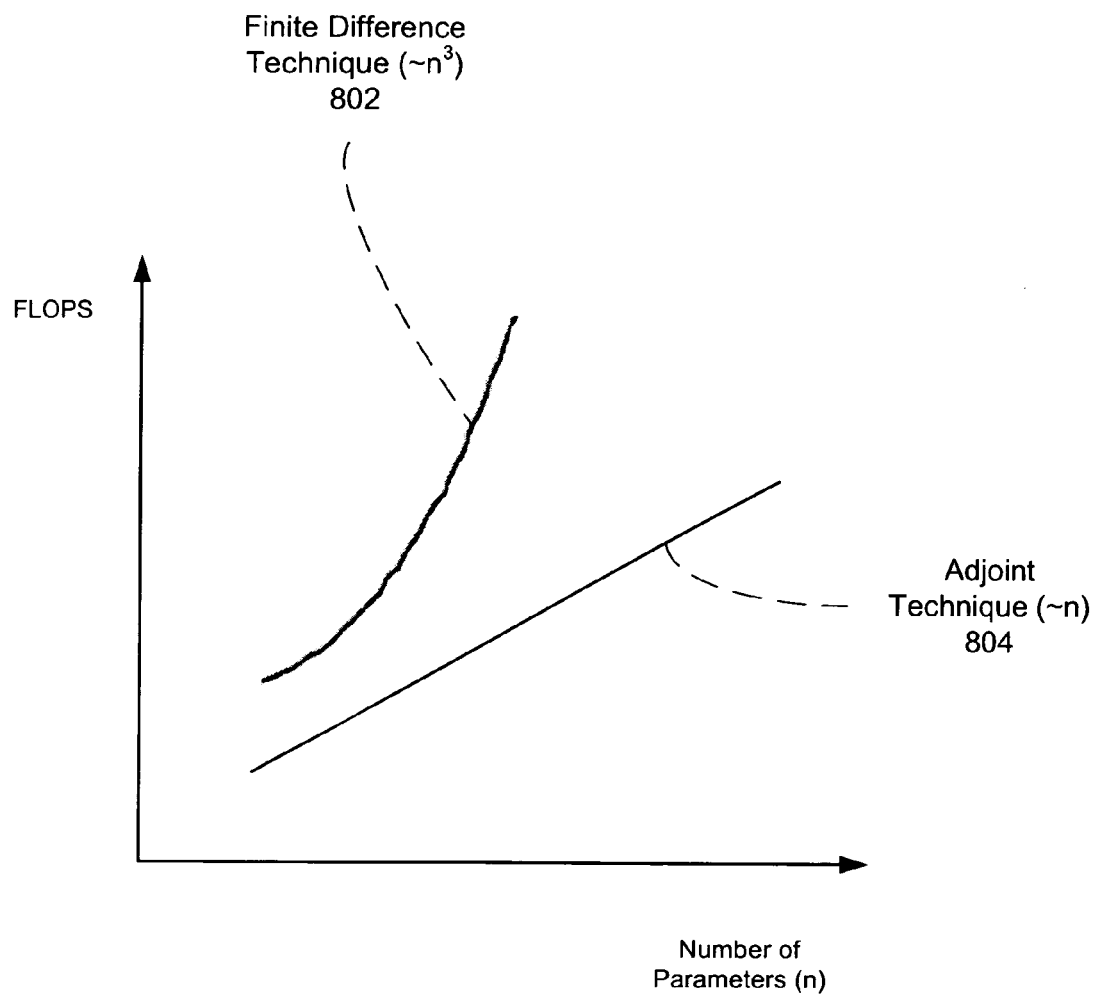
FIG. 8 is a schematic graph comparing the scaling with respect to the number of parameters for the finite difference technique and for the adjoint technique in accordance with an embodiment of the invention.

FIG. 8 is a schematic graph comparing the scaling with respect to the number of parameters for the finite difference technique and for the adjoint technique in accordance with an embodiment of the invention. The graph illustrates roughly the computational time (in floating point operations or FLOPS) per iteration at a given level of accuracy for the techniques as a function of the number of parameters (n) being calculated.

As seen in the graph, computational time for the finite difference technique of the prior art (802) at a given level of accuracy scales in proportion to the third power of the number of parameters. In contrast, the computational time for the "adjoint" technique (804) at a given level of accuracy scales linearly or approximately linearly with the number of parameters in accordance with an embodiment of the present invention. This advantageously enables the adjoint technique to be performed for larger number of parameters. In other words, the adjoint technique scales better with the number of parameters than the prior finite difference technique.

CONCLUSION

The present disclosure provides various new aspects and features over prior techniques. These new aspects and features include at least the following. (i) A frequency domain solution of the adjoint method is formulated using rigorous coupled wave analysis (RCWA). (ii) Parametric derivatives used in optical CD regression are computed using an adjoint method. (iii) Fréchet matrix derivatives in the optical CD adjoint method are computed using a spectral method. (iv) Caching of the Fréchet derivative direction in RCWA. (v) Computation of boundary conditions using S-matrix propagation. (vi) Analytical derivatives of quotients of quadratic forms involving the RCWA state solution are computed. (vii) An analytical form describing a trapezoid is used to produce a local parameter to structural parameter diffeomorphism. (viii) A slabbing algorithm is used to produce a local parameter to structural parameter map. (ix) Measurement sensitivities (derivatives) in a Taylor's expansion are used to perform Numerical Aperture averaging. (x) Measurement sensitivities (derivatives) in a Taylor's expansion are used to compute the measurement spectra at neighboring wavelengths. (xi) The Adjoint solution in the RCWA-based Frequency Domain solution is accelerated using the LU factors from a banded matrix solver. (xii) A time-domain method for computing objective function derivatives is formulated with regard to structural parameters by computing the solution to an adjoint equation. And, (xiii) A time-domain method for computing objective function derivatives is formulated with regard to structural parameters that exploits mirror symmetry to speed up the solution of the adjoint equation.

In various embodiments of the invention, the operations discussed herein (e.g., with reference to FIGS. 2, 6, and 7) may be implemented as hardware (e.g., logic and other circuitry), software, firmware, or combinations thereof, which may be provided as a computer program product, e.g., including a machine-readable or computer-readable medium having stored thereon instructions used to program a computer to perform a process discussed herein. The machine-readable medium may include any suitable storage device.

Reference in the specification to "one embodiment" or "an embodiment" means that a particular feature, structure, or characteristic described in connection with the embodiment may be included in at least an implementation. The appearances of the phrase "in one embodiment" in various places in the specification may or may not be all referring to the same embodiment.

Although embodiments have been described in language specific to geometric features and/or methodological acts, it is to be understood that claimed subject matter may not be limited to the specific features or acts described. Rather, the specific features and acts are disclosed as sample forms of implementing various embodiments. While the invention has been described above in conjunction with one or more specific embodiments, it should be understood that the invention is not intended to be limited to one embodiment. The invention is intended to cover alternatives, modifications, and equivalents as may be included within the spirit and scope of the invention, such as those defined by the appended claims.

What is claimed is:

1. A method of model-based optical metrology to measure a critical dimension of a grating layer, the method comprising:

illuminating an area of a geometrical structure of dispersive materials with incident electromagnetic radiation from an illuminator of a scatterometer apparatus, wherein the incident electromagnetic radiation is polarized;

measuring spectral components of the incident electromagnetic radiation reflected from the area using a detector of the scatterometer apparatus; and using a computer for the scatterometer apparatus to determine parameter values for the semiconductor structure that minimize an objective function J which depends on differences between the measured spectral components and computed spectral components based on a parameterized geometrical model of the geometrical structure, wherein steps for determining the parameter values that minimize the objective function include:

computing $\nabla_p J$ where p is a parameterized vector of the parameter values, wherein the parameter values comprise $f$ and h, where h is a height of the grating layer, and $f$ is a critical dimension fraction comprising the critical dimension divided by a pitch of the grating layer.

2. The method of claim 1, further comprising:

computing a solution to state equations driven by a function representing the incident electromagnetic radiation, wherein the state equations are derived from Maxwell's equations with dispersive materials, and wherein the solution to the state equations provides reflection and transmission coefficients and coefficients describing boundary conditions.

3. The method of claim 2, wherein computing the solution to the state equations is performed in the frequency domain.

4. The method of claim 3, wherein computing the solution to the state equations is performed using a banded matrix linear system solver.

5. The method of claim 4, further comprising:

computing a solution to an adjoint to the state equations, wherein the adjoint to the state equations has a source function which is a derivative of a measurement function as a function of the solution of the state equations, wherein computing the solution to the adjoint to the state equations is performed by re-using LU-decomposition factors from the banded matrix linear system solver.

6. The method of claim 1, wherein the objective function J comprises $$\frac{1}{2}(\alpha - \alpha_0)^2 + \frac{1}{2}(\beta - \beta_0)^2$$

where $\alpha_0$ and $\beta_0$ are the measured spectral components, and $\alpha$ and $\beta$ are the computed spectral components.

7. The method of claim 6, wherein $\alpha$ is proportional to $x_m^H cc^T x_m - x_e^H ss^T x_e$, and $\beta$ is proportional to $2\Re(x_e^H sc^T x_m)$, where $x_m$ is a magnetic state vector, $x_e$ is an electric state vector, c and s are vectors which are proportional to vector $e_{r0}$ which extracts the zeroth order reflection coefficient from the state vectors $x_m$ and $x_e$.

8. The method of claim 7, wherein the vector $c=\cos(\eta)e_{r0}$ and the vector $s=\sin(\eta)e_{r0}$, where $\eta$ is an analyzer angle.

9. The method of claim 2, wherein the steps for determining the parameter values that minimize the objective function further include:

computing a mapping between derivatives of the state equations with respect to the parameter values and derivatives of the state equations with respect to geometric parameters, wherein the geometric parameters describe geometric shapes within the geometrical structure.

10. The method of claim 9, wherein the geometric parameters comprise trapezoid height, width and wall angle.

11. The method of claim 5, wherein the computation of the solution to the state equations is performed in the time domain.

12. The method of claim 11, wherein the steps for determining the parameter values that minimize the objective function further include:

computing a derivative of the objective function with respect to control parameters.

13. The method of claim 12, wherein the computation of the derivative of the objective function with respect to the control parameters involves computing an inner product between the state and adjoint equations.

14. The method of claim 1, wherein the grating layer is patterned along one dimension.

15. The method of claim 1, wherein the grating layer is patterned in two dimensions.

16. The method of claim 11, where the geometrical structure possesses mirror symmetry, and the adjoint equations are computed from the state equations by conjugation—with no additional, separate solution of Maxwell's Equations.

17. An apparatus for optical metrology for measuring a critical dimension of a grating layer, the apparatus comprising:

a polarized illuminator configured to illuminate an area of a geometrical structure of dispersive materials with incident polarized electromagnetic radiation;

a detector for measuring spectral components of the incident electromagnetic radiation reflected from the area; and a data processing system comprising computer-readable code configured to determine parameter values that minimize an objective function J which depends on differences between the measured spectral components and computed spectral components based on a parameterized model of the geometrical structure, wherein the objective function J comprises $$\frac{1}{2}(\alpha - \alpha_0)^2 + \frac{1}{2}(\beta - \beta_0)^2$$

where $\alpha_0$ and $\beta_0$ are the measured spectral components, and $\alpha$ and $\beta$ are the computed spectral components, and computer-readable code configured to compute $\nabla_p J$, where p is a parameterized vector of the parameter values, wherein the parameter values include at least $f$ and h, where $f$ is a critical dimension fraction comprising the critical dimension divided by a pitch of the grating layer, and h is a height of the grating layer, wherein the grating layer comprises a non-uniform index of refraction.

18. The apparatus of claim 17, wherein the data processing system further comprises:

computer-readable code configured to compute a solution to state equations driven by a function representing the incident electromagnetic radiation, wherein the state equations are derived from Maxwell's equations with dispersive materials, wherein said code configured to compute the solution to the state equations is configured to make computations in a frequency domain.

19. The apparatus of claim 18, wherein the data processing system further comprises:

computer-readable code configured to compute a solution to an adjoint to the state equations, wherein the adjoint to the state equations has a source function which is a derivative of a measurement function as a function of the solution of the state equations, wherein the code configured to compute the solution to the state equations includes code configured to use a banded matrix linear system solver, and wherein the code configured to compute the adjoint to the state equations includes code configured to re-use LU-decomposition factors from the banded matrix linear system solver.

20. The apparatus of claim 17, wherein $\alpha$ is proportional to $x_m^H cc^T x_m - x_e^H ss^T x_e$, and $\beta$ is proportional to $2\Re(x_e^H sc^T x_m)$, where $x_m$ is a magnetic state vector, $x_e$ is an electric state vector, c and s are vectors which are proportional to vector $e_{r0}$ which extracts the zeroth order reflection coefficient from the state vectors $x_m$ and $x_e$.

21. The apparatus of claim 20, wherein the vector $c=\cos(\eta)e_{r0}$ and the vector $s=\sin(\eta)e_{r0}$, where $\eta$ is an analyzer angle.

22. The apparatus of claim 20, wherein the data processing system further comprises:
  computer-readable code configured to compute a mapping between derivatives of the state equations with respect to the parameter values and derivatives of the state equations with respect to geometric parameters, wherein the geometric parameters describe geometric shapes within the geometrical structure.

23. The apparatus of claim 22, wherein the geometric parameters comprise trapezoid height, width and wall angle.

24. The apparatus of claim 19, wherein the computer-readable code configured to compute the solution to the state equations is configured to make computations in a time domain.

25. The apparatus of claim 24, wherein the data processing system further comprises:
  computer-readable code configured to compute a derivative of the objective function with respect to control parameters.

26. The apparatus of claim 25, wherein the code configured to compute the derivative of the objective function includes code configured to compute an inner product between the state and adjoint equations.

27. The apparatus of claim 17, wherein the grating layer is patterned along one dimension.

28. The apparatus of claim 17, wherein the grating layer is patterned in two-dimensions.

29. A method for estimating a critical dimension of a grating layer from spectroscopic measurements, the method comprising:
  using an illuminator of a scatterometer apparatus to illuminate an area of a geometrical structure of dispersive materials with incident electromagnetic radiation;
  measuring spectral components of the incident electromagnetic radiation reflected from the area using a detector of the scatterometer apparatus;
  using a computer for the scatterometer apparatus to compute a solution to state equations driven by a function representing the incident electromagnetic radiation, wherein the state equations are derived from Maxwell's equations with dispersive materials;
  using the computer for the scatterometer apparatus to compute a solution to an adjoint to the state equations, wherein the adjoint to the state equations has a source function which is a derivative of a measurement function as a function of the solution of the state equations; and
  using the computer for the scatterometer apparatus to determine parameter values for the semiconductor structure that minimize an objective function J which depends on differences between the measured spectral components and computed spectral components based on a parameterized geometrical model of the geometrical structure,
  wherein steps for determining the parameter values that minimize the objective function include:
  computing $\nabla_p J$ where p is a parameterized vector of the parameter values, wherein the parameter values comprise $f$ and h, where h is a height of the grating layer, and $f$ is a critical dimension fraction comprising the critical dimension divided by a pitch of the grating layer.

30. The method of claim 29, wherein regression is used to compute the solution to the state equations and hence to estimate the critical dimension.

31. The method of claim 29, wherein a library is produced and then used to compute the solution to the state equations and hence to estimate the critical dimension.

32. The method of claim 29, where a combination of a library and regression are used to compute the solution to the state equations and hence to estimate the critical dimension.

33. The method of claim 29, wherein time to compute each iteration of the solution to the state equations at a given level of accuracy scales slower with an increasing number of parameters than computing each iteration of the solution to the state equations at the given level of accuracy by finite difference derivatives.

34. The method of claim 29, wherein with an increasing number of parameters N, a computation time per iteration at a given level of accuracy increases at a rate slower than N to the third power.

35. The method of claim 34, wherein the computation time per iteration at the given level of accuracy increases linearly with N.

* * * * *